(12) United States Patent
Chopra et al.

(10) Patent No.: US 11,980,709 B2
(45) Date of Patent: May 14, 2024

(54) SYSTEM AND RELATED METHODS FOR FAT HARVESTING

(71) Applicant: Chopra Gryskiewicz, LLC, Burnsville, MN (US)

(72) Inventors: Karan Chopra, Minneapolis, MN (US); Joseph M. Gryskiewicz, Edina, MN (US); Richard A. Thompson, St. Louis Park, MN (US); Reed O. Saunders, Minneapolis, MN (US); Evan M. Leingang, Plymouth, MN (US); Thomas A. Tedham, Eden Prairie, MN (US); Mohamed A. Mohamed, Minneapolis, MN (US); Jacob T. Wilson, Blaine, MN (US); Brett J. Herdegen, Lauderdale, MN (US); Jason N. Scherer, Woodbury, MN (US); Landon Hove Dinger, Minneapolis, MN (US); Justin A. Barbot, Bottineau, ND (US)

(73) Assignee: Chopra Gryskiewicz, LLC, Burnsville, MN (US)

( * ) Notice: Subject to any disclaimer, the term of this patent is extended or adjusted under 35 U.S.C. 154(b) by 0 days.

(21) Appl. No.: 18/143,779

(22) Filed: May 5, 2023

(65) Prior Publication Data
US 2023/0277752 A1   Sep. 7, 2023

Related U.S. Application Data

(63) Continuation of application No. 17/677,664, filed on Feb. 22, 2022, now Pat. No. 11,679,198.
(Continued)

(51) Int. Cl.
*A61M 1/00* (2006.01)
*A61M 39/22* (2006.01)
(Continued)

(52) U.S. Cl.
CPC ............. *A61M 1/89* (2021.05); *A61M 1/67* (2021.05); *A61M 1/87* (2021.05); *A61M 39/223* (2013.01);
(Continued)

(58) Field of Classification Search
CPC ............ A61M 1/89; A61M 1/67; A61M 1/87; A61M 1/00; A61M 27/00; A61M 39/223;
(Continued)

(56) References Cited

U.S. PATENT DOCUMENTS

| 3,941,317 A | 3/1976 | Kanor |
| 6,020,196 A | 2/2000 | Hu et al. |

(Continued)

FOREIGN PATENT DOCUMENTS

| AU | 2017204616 | 3/2020 |
| WO | WO 2017/189918 | 11/2017 |

OTHER PUBLICATIONS

U.S. Appl. No. 63/175,660, filed Apr. 16, 2023, Khouri et al.
(Continued)

*Primary Examiner* — Catharine L Anderson
*Assistant Examiner* — Ilya Y Treyger
(74) *Attorney, Agent, or Firm* — Fish & Richardson P.C.

(57) ABSTRACT

A fat harvesting systems and related methods of harvesting and reinjecting fat that provides a medical professional with multiple technique options. Harvested fat can be subjected to a variety of pre-reinjection preparation steps within a single, self contained reservoir such that the potential for contaminating the harvested fat is avoided. The fat harvesting system can be completely self-contained kit requiring no additional external systems or alternatively, can utilize available surgical suite systems, for example, vacuum to successfully harvest, prepare and reinject fat cells. The fat harvesting system can size harvested fat cells so as to be (Continued)

especially desirable for different injection locations in the body. The fat harvesting system is a single use, disposable system that requires no sterilization equipment and recovered and sized fat cells are maintained in a sanitary environment so as to avoid contamination that could result in having to discard recovered fat cells.

14 Claims, 37 Drawing Sheets

Related U.S. Application Data

(60) Provisional application No. 63/180,933, filed on Apr. 28, 2021.

(51) Int. Cl.
*A61B 5/05* (2021.01)
*A61H 1/00* (2006.01)
*A61M 27/00* (2006.01)

(52) U.S. Cl.
CPC ... *A61M 2039/229* (2013.01); *A61M 2202/08* (2013.01)

(58) Field of Classification Search
CPC ........ A61M 2039/229; A61M 2202/08; A61N 1/30; A61B 17/20; A61B 5/05; A61H 1/00
See application file for complete search history.

(56) References Cited

U.S. PATENT DOCUMENTS

| | | | |
|---|---|---|---|
| 6,800,186 B1* | 10/2004 | Forand | C25D 5/67 205/93 |
| 7,501,115 B2 | 3/2009 | Fraser et al. | |
| 7,588,732 B2* | 9/2009 | Buss | A61M 1/85 210/94 |
| 7,780,649 B2* | 8/2010 | Shippert | A61M 1/79 604/218 |
| 8,100,874 B1 | 1/2012 | Jordan et al. | |
| 8,202,493 B2 | 6/2012 | Buss | |
| 8,360,102 B2 | 1/2013 | Khouri et al. | |
| 8,366,694 B1 | 2/2013 | Jordan | |
| 8,512,695 B2 | 8/2013 | Austen, Jr. | |
| 9,814,810 B2 | 11/2017 | Cucin | |
| 10,039,886 B2 | 8/2018 | Pilkington et al. | |
| 10,172,981 B2 | 1/2019 | Gourlay | |
| 10,183,101 B2 | 1/2019 | Conlan et al. | |
| 10,184,110 B2 | 1/2019 | Austen, Jr. | |
| 10,188,777 B2 | 1/2019 | Conlan et al. | |
| 10,279,325 B1 | 5/2019 | Crombie et al. | |
| 10,702,629 B2 | 7/2020 | Pilkington et al. | |
| 10,702,656 B2 | 7/2020 | Pilkington et al. | |
| 10,786,791 B1 | 9/2020 | Crombie et al. | |
| 10,927,347 B2 | 2/2021 | Pilkington et al. | |
| 11,013,838 B2 | 5/2021 | Hagarty et al. | |
| 11,672,557 B2 | 6/2023 | Khouri et al. | |
| 11,679,198 B2 | 6/2023 | Chopra et al. | |
| 2005/0171487 A1 | 8/2005 | Haury et al. | |
| 2009/0239299 A1 | 9/2009 | Buss | |
| 2009/0287190 A1 | 11/2009 | Shippert | |
| 2014/0081237 A1 | 3/2014 | Wolters et al. | |
| 2014/0236294 A1 | 8/2014 | Khouri | |
| 2015/0090652 A1* | 4/2015 | Hensler | A61M 1/60 210/232 |
| 2015/0209565 A1 | 7/2015 | Dauvister et al. | |
| 2015/0231641 A1 | 8/2015 | Temolada | |
| 2017/0203040 A1 | 7/2017 | Conlan et al. | |
| 2017/0368226 A1 | 12/2017 | Pilkington et al. | |
| 2018/0133377 A1 | 5/2018 | Khouri et al. | |
| 2019/0105433 A1 | 4/2019 | Hagarty et al. | |
| 2019/0125971 A1 | 5/2019 | Bachrach et al. | |
| 2019/0143005 A1 | 5/2019 | Conlan et al. | |
| 2020/0054824 A1 | 2/2020 | Hagarty | |
| 2020/0346208 A1 | 11/2020 | Rubin | |
| 2021/0353850 A1 | 11/2021 | Khouri et al. | |
| 2022/0000603 A1 | 1/2022 | Khouri | |
| 2022/0039937 A1 | 2/2022 | Khouri et al. | |
| 2022/0347374 A1 | 11/2022 | Chopra et al. | |

OTHER PUBLICATIONS

Alexander et al., "Autologous fat grafting: use of closed syringe microcannula system for enhanced autologous structural grafting," Clinical, Cosmetic and Investigational Dermatology, Apr. 2013, 91-102.

manualslib.com, "Allegran Resolve, System Instructions for Use," Jun. 2018, 2 pages.

Mestak et al., "Breast reconstruction after a bilateral mastectomy using the BRAVA expansion system and fat grafting," Plastic and Reconstructive Surgery Global Open, Nov. 2013, 1(8).

PCT International Preliminary Report on Patentability in International Appln. No. PCT/US2022/026411, dated Oct. 24, 2023, 13 pages.

PCT International Search Report and Written Opinion in International Appln. No. PCT/US2022/026411, dated Sep. 6, 2022, 16 pages.

PCT Invitation to Pay Additional Fees and, Where Applicable, Protest Fee for International Application No. PCT/US2022/026411, dated Jun. 9, 2022, 2 pages.

sientra.com, "Viality, Lipoaspirate Wash System," Feb. 2023, 3 pages.

\* cited by examiner

SYSTEM AND RELATED METHODS FOR FAT HARVESTING

PRIORITY CLAIM

The present application is a continuation of U.S. application Ser. No. 17/677,664, filed Feb. 22, 2022, which claims priority to U.S. Provisional Application Ser. No. 63/180,933, filed Apr. 28, 2021 and entitled "SYSTEM AND RELATED METHODS FOR FAT HARVESTING", which is hereby incorporated by reference in its entirety.

TECHNICAL FIELD

The present invention is directed to fat harvesting for transfer and reinjection into desired body locations. More specifically, the present invention is directed to a self-contained fat harvesting system with an integrated sizing system for fat preparation prior to reinjection.

BACKGROUND

Fat harvesting is a common cosmetic surgery procedure where fat cells are harvested from body locations having excess fat, such as, for example, the outer thighs and subsequently transferring/reinjecting the fats into other body locations such as, for example, the face, breasts, and buttocks. Generally, fat transfer can be used simply to increase the size/volume of a body feature or alternatively, can be used to improve body contours, fill depressions or to revise the appearance of scars. As fat harvesting involves using autologous fat, there is a reduced chance of allergic reactions that may be present with foreign substances, such as, implants and dermal fillers.

SUMMARY

A fat harvesting system and related methods of harvesting and reinjecting fat comprises a kit providing multiple technique options based upon the individual preferences of a medical professional performing the fat harvesting. During use of the fat harvesting system, harvested fat can be subjected to a variety of pre-injection preparation steps within a single, self-contained reservoir such that the potential for contaminating the harvested fat is avoided. In certain embodiments of the fat harvesting system, the fat harvesting system is a completely self-contained kit requiring no additional storage or treatment components or external systems, for example, vacuum to successfully harvest, prepare and reinject fat cells. Alternatively, and based on the preferred practices of the medical professional performing the fat harvesting, the fat harvesting system of the present invention can be utilized in an office environment or in an operating room where an available suction or vacuum source can be utilized. The fat harvesting system of the present invention can size fat cells so as to be especially desirable for different injection locations in the body. The fat harvesting system of the present invention is a sterilized, single use, disposable system that requires no sterilization equipment and the recovered and sized fat cells are always contained in a sanitary environment so as to avoid contamination that could result in having to discard recovered fat cells.

In one aspect, the present invention is directed to a device for harvesting and reinjecting fat cells. The device generally comprises a device reservoir in which fat cells are recovered, retained and processed for reinjection such that the potential of contamination during transfer to external components is eliminated. Generally, the fat harvesting device is capable of self-contained operation without the use of any external collection device or suction source such that device can be utilized outside of a surgical suite setting. Depending upon the preferred technique of the medical professional, the fat harvesting device can be utilized in conjunction with external collection devices or suction sources during one or more steps of the fat collection, processing and reinjection steps.

In one aspect of the present invention, a method of harvesting and reinjecting fat cells can comprise a first step of harvesting fat cells from a body location containing excess fat. Once the fat cells have been harvested, the fat cells residing in a device reservoir can be decanted to separate an "oily" layer containing the fat cells from an aqueous layer containing blood, serum and other biological components. Once the decanting step has been accomplished in the device reservoir, the aqueous layer can be expelled from the device reservoir such that only the oily layer containing the fat cells remains within the device reservoir. Next, a washing step can be performed on the fat cells by introducing saline into the device reservoir either through a distal valve or through a side port on the harvesting device, whereby a plunger assembly can be used to pass the saline through the fat cells. Following the washing step, the decanting step can be repeated to separate and remove the saline from the device reservoir and "dry" the fat cells. Once the fat cells have been washed, the fat cells can be sized or "morcellized" by directing a sizing screen through the device reservoir such that the fat cells achieved the medical professional's desired size for reinjection. Finally, the separated, washed and sized fat cells can be ejected from the device reservoir and injected into the desired body location. At various times of the disclosed method, agglomerated fat cells or other biological materials can cause elements of the harvesting device to become clogged or plugged such that one or more of the steps of decanting, washing and sizing is negatively impacted. As such, the method can further comprise one or more steps of unclogging and clearing the harvesting device while retaining the recovered fat cells within the device reservoir.

In one aspect of the disclosed method, a harvesting step can be performed using one of three different techniques as selected by the medical professional. In one instance, the medical professional can utilize a plunger assembly on the fat harvesting device to induce a vacuum condition at a cannula tip to draw fat cells into the device reservoir such that no external vacuum source is required. Alternatively, the medical professional can attach a vacuum line to a vacuum connector on the fat harvesting device to draw the fat cells into the device reservoir. In another alternative arrangement, the medical professional can utilize a powered liposuction device to harvest the fat cells from the body, whereby the powered liposuction device can be attached to a cannula connector on the harvesting device to introduce the fats cells in the device reservoir.

In another aspect of the disclosed method, a decanting step can be performed for separating an oily layer contained the harvested fat cells from an aqueous layer containing blood, serum and other biological materials. Generally, the fat harvesting device with the recovered fat cells contained with the device reservoir, can be placed into a vertical disposition, for example, by placing and retaining the fat harvesting device on a stand that can be included as part of a kit with the fat harvesting device.

In another aspect, the medical professional can choose one of three techniques for expelling and removing the separated aqueous layer from the device reservoir based upon the preference of the medical professional as well as removal speed. In one technique, the medical professional can open a rotatable floor cap that allows the heavier aqueous phase to flow out the bottom of the floor cap. In another technique, the medical professional can open a manual valve to allow the heavier aqueous phase to gravity flow through a valve port. Finally, the medical professional can make use of an available suction source to draw the heavier aqueous phase through a side port on the harvesting device. Generally, using an external suction source will be the fastest technique while using gravity flow through the rotatable floor cap or valve port will be slower. Due to the increased cross-section of the floor cap opening, flow through the rotatable floor cap will generally be faster than gravity flow through the valve port. When utilizing an external suction/vacuum source, a plunger and sizing assembly can be locked into position within the device reservoir to prevent movement of the plunger and sizing assemblies as suction is applied.

In another aspect, the medical professional can wash a retained oily layer of recovered fat cells with saline to remove additional water soluble biological materials from the oily layer. Generally, the saline can be introduced into the device reservoir through a side port or through a valve port. With the saline introduced into the device reservoir, a piston member can be directed back and forth through the device reservoir to mix and wash the oily layer with the saline. Following washing, the decanting and expelling steps can be repeated to remove the saline and water soluble biological components from the device reservoir. The washing step can be repeated as many times as desired by the medical professional.

In another aspect, the washed fat cells can be sized by the medical professional within the device reservoir. Medical professionals may have personal preferences as to the sizes of reinjected fat cells based on, for example, the body location in which fat cells are to be reinjected. Generally, the medical professional can utilize a sizing plunger to advance a sizing screen through the device reservoir. The sizing screen generally comprises a mesh or perforated screen having desired mesh or pore sizes. As the sizing screen passes through the device reservoir, the fat cells are essentially morcellized and forced through the mesh or pores. In some instances, the sizing screen can be segmented to have two or more distinct screen sections having different mesh or pore sizes. As such, the medial professional can choose to start with a larger mesh or pore size and then adjust the sizing screen to go to a smaller mesh or pore size and repeat the morcellization of the fat cells. In this way, the medical professional chooses the size of the fat cells for reinjection without the fat cells ever being removed from the device reservoir.

In another aspect, the decanted, washed and sized fat cells are reinjected into a desired body location by the medical professional. Generally, the medical professional can attach an injection cannula to a valve port on the harvesting device and utilizes the plunger assembly to direct the fat cells out of the device reservoir, through the injection cannula and into the desired body location. Alternatively, a secondary injection syringe can be filled with the decanted, washed and sized fat cells by attaching the secondary injection syringe to the valve port or to a side port on the harvesting device and transferring the decanted, washed and sized fat cells from the harvesting device to the secondary injection syringe, which is subsequently detached and utilized by the medical professional.

In yet another aspect of the disclosed method, various components in fluid communication with the device reservoir can become clogged or plugged with biological removal making performance of the expelling, washing and sizing steps slower and more difficult to perform. As such, one or more unclogging steps can be accomplished during the method of harvesting fat cells while still retaining the recovered fat cells within the device reservoir. For instance, plugging of the manual valve or rotatable floor cap can be cleared by twisting off a floor cap such that the material causing the plugging can be physically removed. In addition, plugging of the side port can be cleared by physically advancing the plunger assembly back and forth across a side port aperture in the device reservoir, whereby a plunger seal can physically remove any material blocking the side port. Finally, the sizing screen can comprise a rotatable wipe blade that can be rotatably manipulated to physically clear the sizing screen of any biological material accumulated on upper and lower surfaces of the sizing screen.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
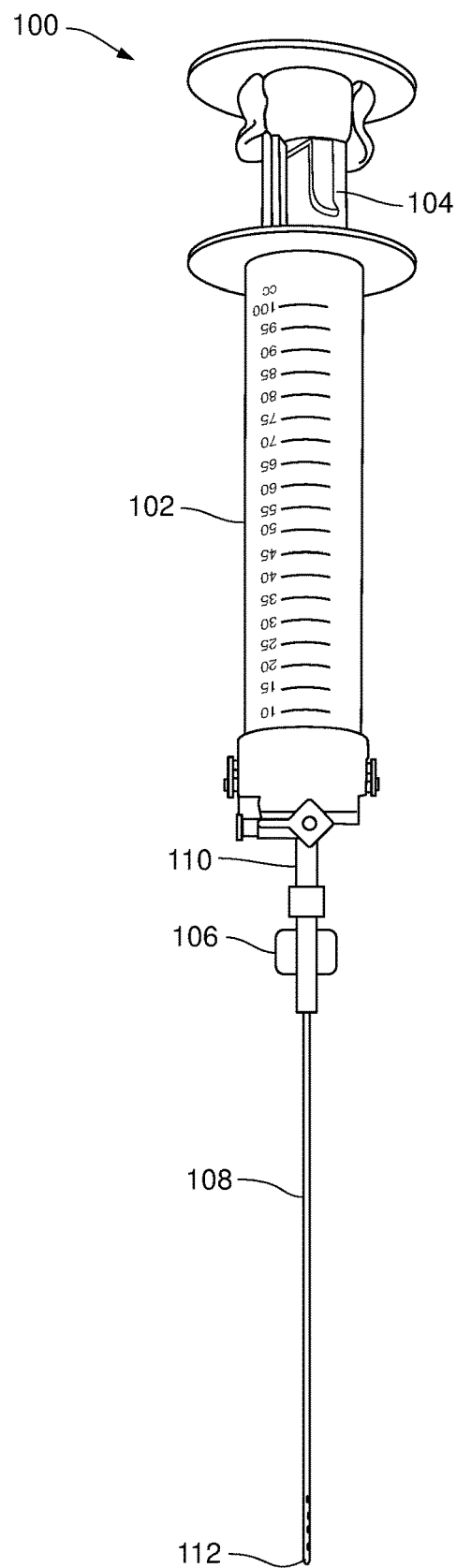
FIG. 1 is a side view of a fat harvesting system according to a representative embodiment of the present invention.

While various embodiments are amenable to various us and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Figure 2:
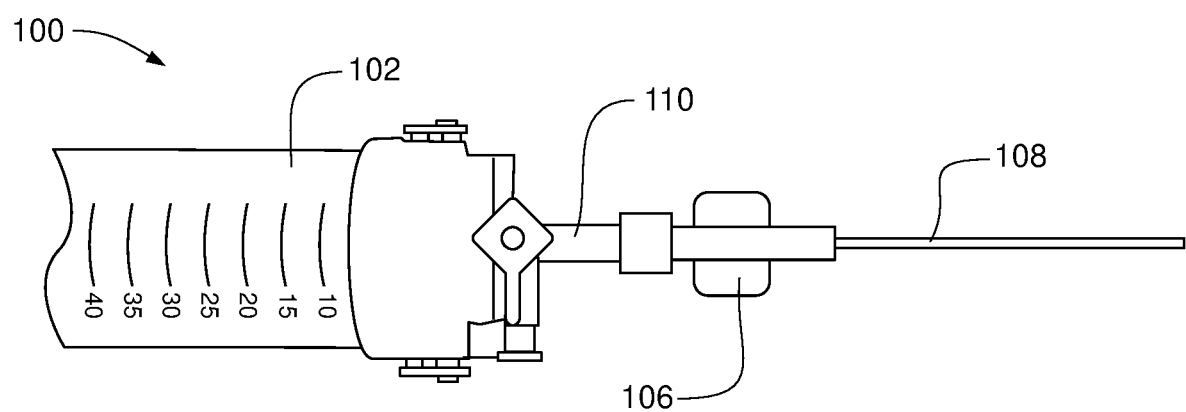
FIG. 2 is a detailed side view of a portion of the fat harvesting system of FIG. 1.
Figure 3:
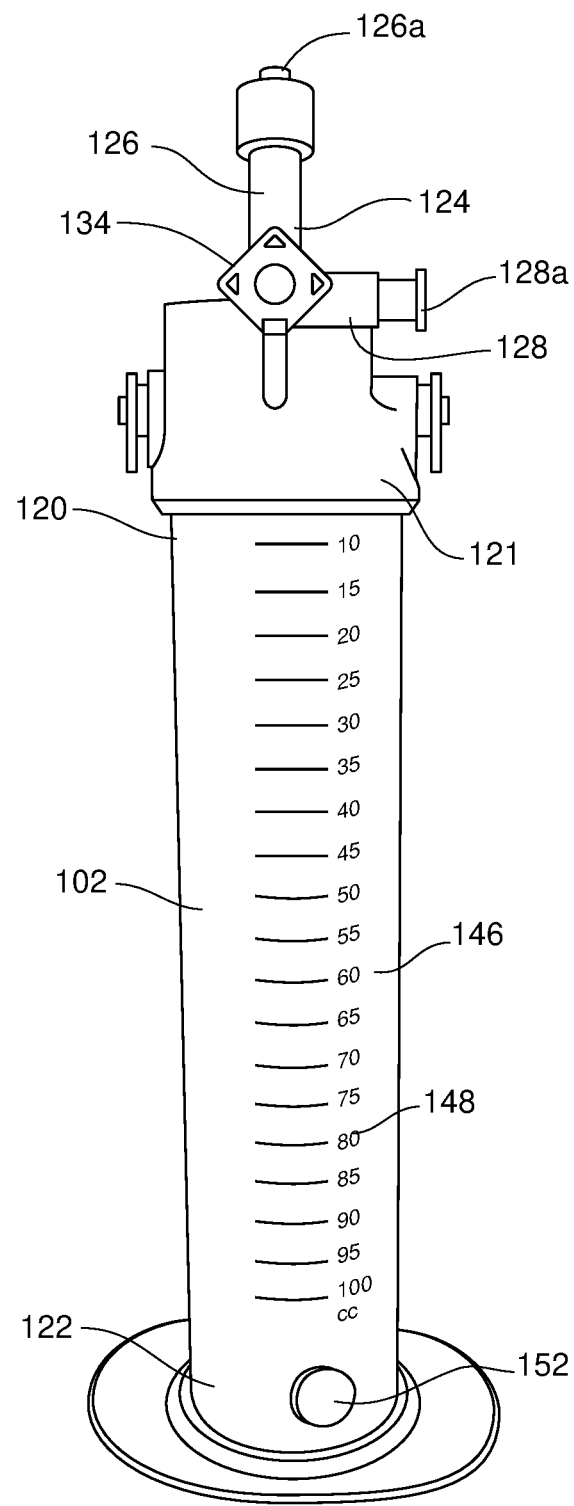
FIG. 3 is a side view of a cylindrical body of the fat harvesting system of FIG. 1 with a valve member closing off a body interior of the cylindrical body.
Figure 4:
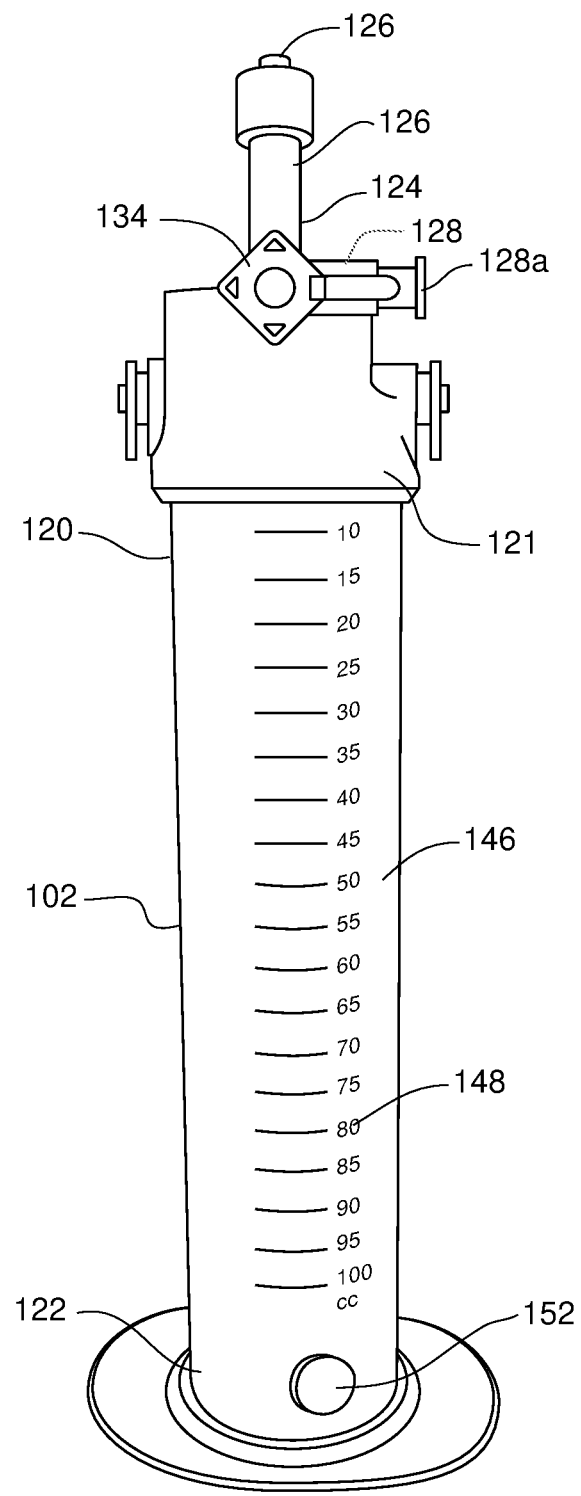
FIG. 4 is a side view of the cylindrical body of FIG. 3 with the valve member closing off a second conduit.
Figure 5:
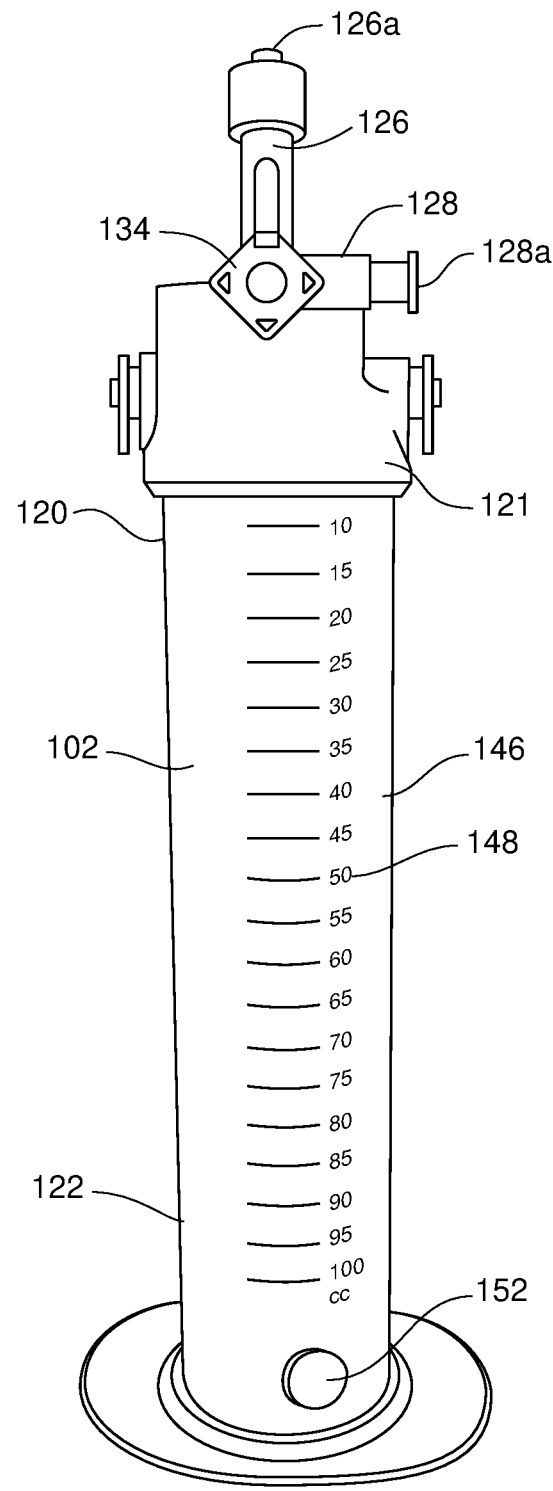
FIG. 5 is a side view of the cylindrical body of FIG. 3 with the valve member closing off a first conduit.
Figure 6:
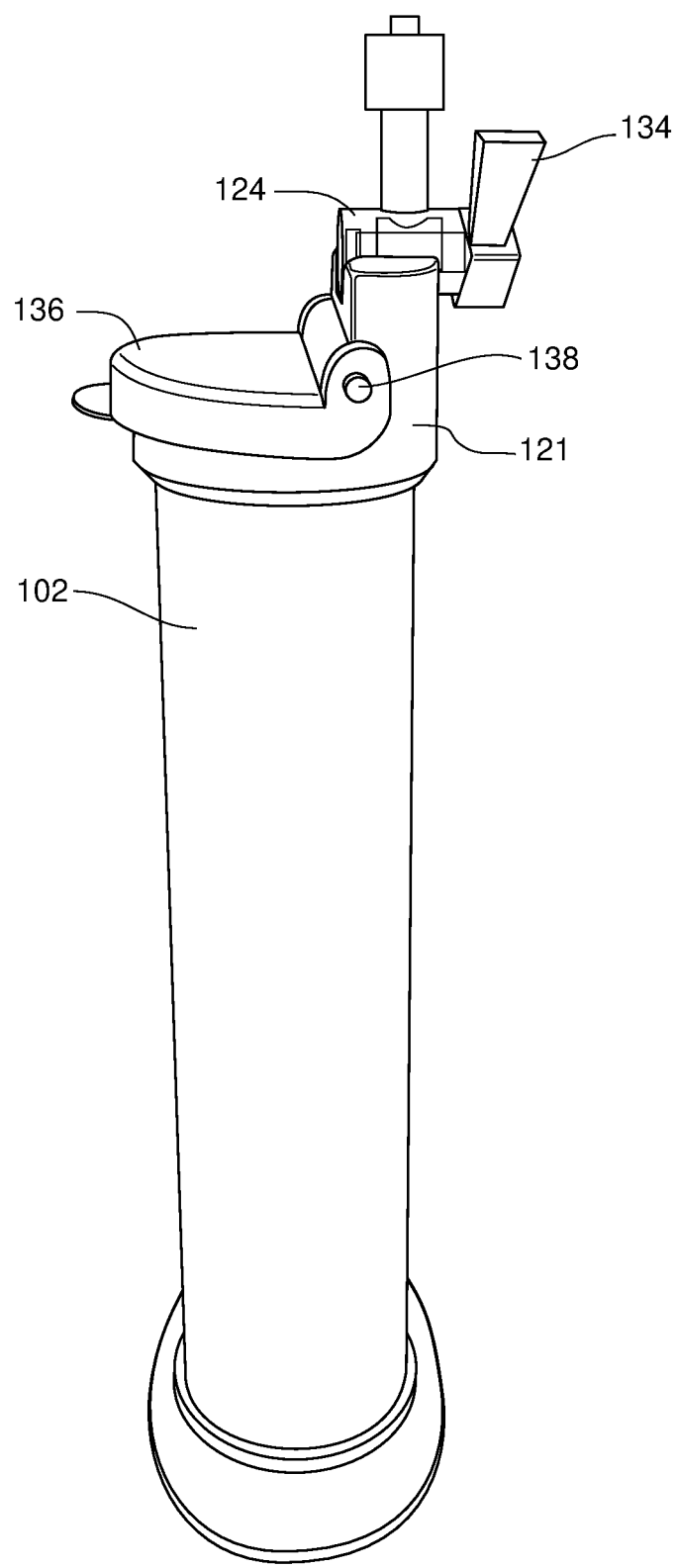
FIG. 6 is a side view of the cylindrical body of FIG. 3 with a rotatable cover in a closed position.
Figure 7:
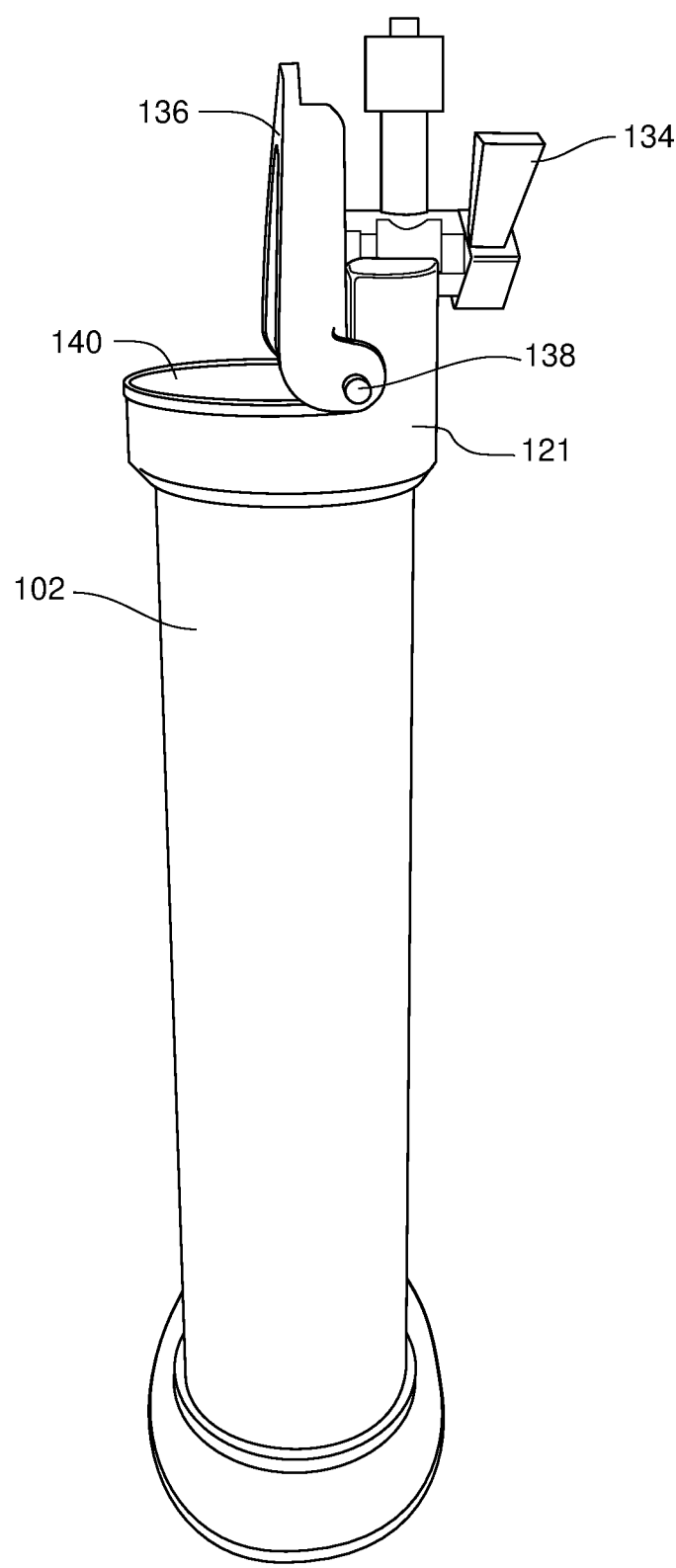
FIG. 7 is a side view of the cylindrical body of FIG. 3 with the rotatable cover in an open position.
Figure 8:
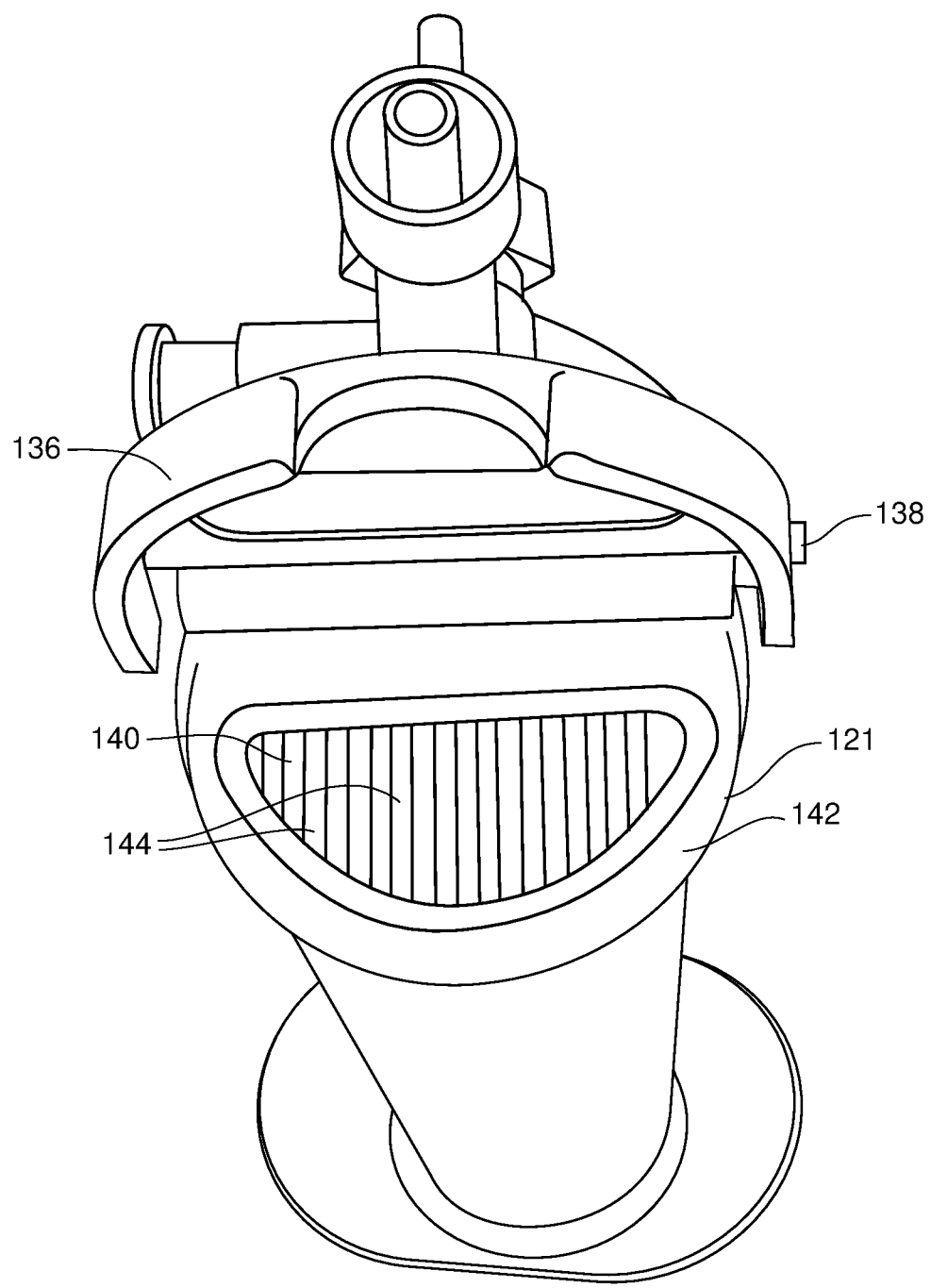
FIG. 8 is an end view of the cylindrical body of FIG. 3 with the rotatable cover in the open position.
Figure 9A:
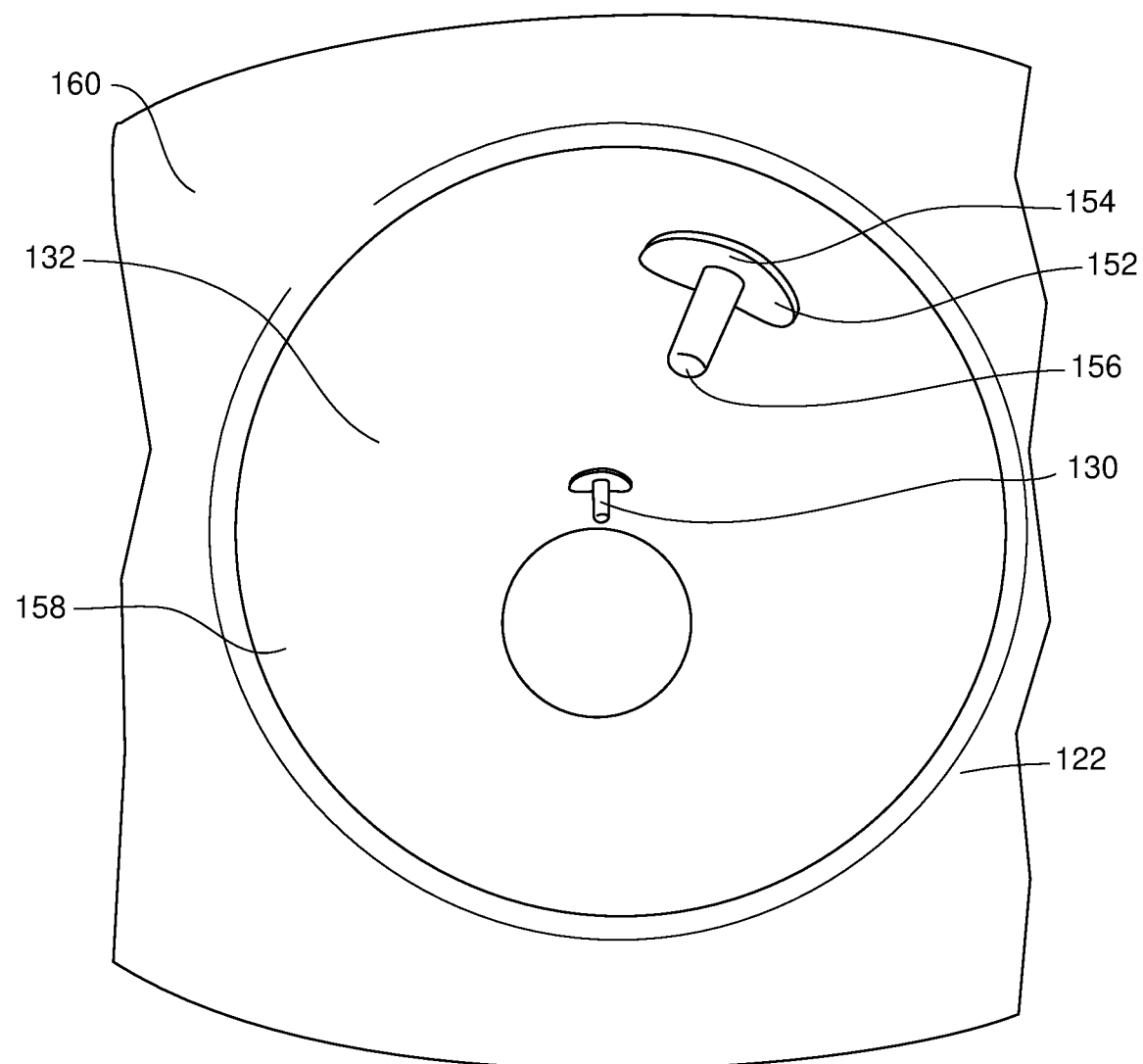
FIG. 9A is an end view of cylindrical body of FIG. 3 illustrating a body interior.
Figure 9B:
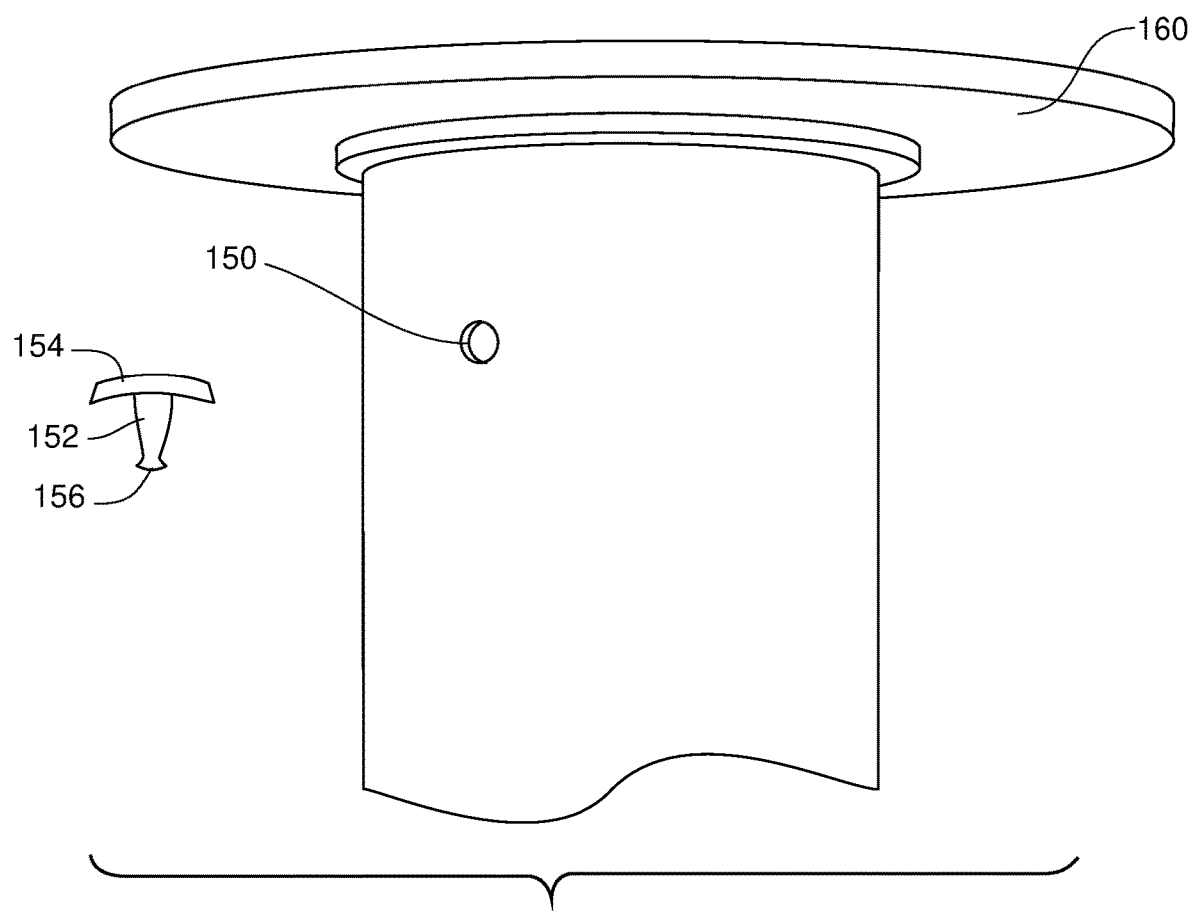
FIG. 9B is an enlarged, partially exploded, side view of the cylindrical body of FIG. 3.

Referring now to FIGS. 1 and 2, a representative fat harvesting system 100 of the present invention generally comprises a cylindrical body 102, a plunger assembly 104 and a harvesting cannula 106. Generally, the fat harvesting system 100 can be fabricated of materials compatible with and approved for use in medical procedures involving humans. Representative materials can comprise metals such as, for example, stainless steel and polymers such as, for example, polypropylene, polyethylene, polyvinyl chloride, polyamide, polycarbonate and the like.

With reference to FIG. 1, harvesting cannula 106 generally comprises a harvesting needle 108 and a connector 110 such as, for example, a luer-lock connector. Harvesting cannula 106 generally defines a continuous lumen (not shown) between a needle tip 112 and the connector 110. Though said continuous lumen is not illustrated, it will be understood that harvesting cannula 106 can utilize a conventional cannula design as would be understood by a person of ordinary skill in the art.

Referring now to FIGS. 3, 4, 5, 6, 7, 8, 9A and 9B, cylindrical body 102 is generally defined between a treatment end 120 and an open end 122. Treatment end 120 generally includes a floor cap 121 for closing off the treatment end 120. Floor cap 121 generally includes a flow conduit 124 including a first conduit 126, a second conduit 128, each including an associated conduit connector 126a, 128a. Flow conduit 124 is operably mounted into a cylinder floor aperture 130 defined in the floor cap 121 such that the flow conduit 124 is operably, fluidly coupled with a body interior 132. Flow conduit 124 includes a manual valve member 134 or selectively opening and closing access between the first conduit 126, the second conduit 128 and the body interior 132. Floor cap 121 further comprises a rotatable cover 136 rotating about a cover hinge 138 to selectively allow flow through a porous floor screen 140 covering a floor opening 142 defined in the floor cap 121. The floor opening 142 can comprise one or more screen support members 144 over which the porous floor screen 140 can be mounted and supported. Cylindrical body 102 generally defines a body wall 146 that can include volumetric indicia 148 and a side aperture 150 in which a locking member 152 is mounted therein. Locking member 152 can include a tab portion 154 and a locking post 156 that extends through the side aperture 150 and projects into the body interior 132. Open end 122 generally defines a plunger aperture 158 and a body grip 160.

Figure 10:
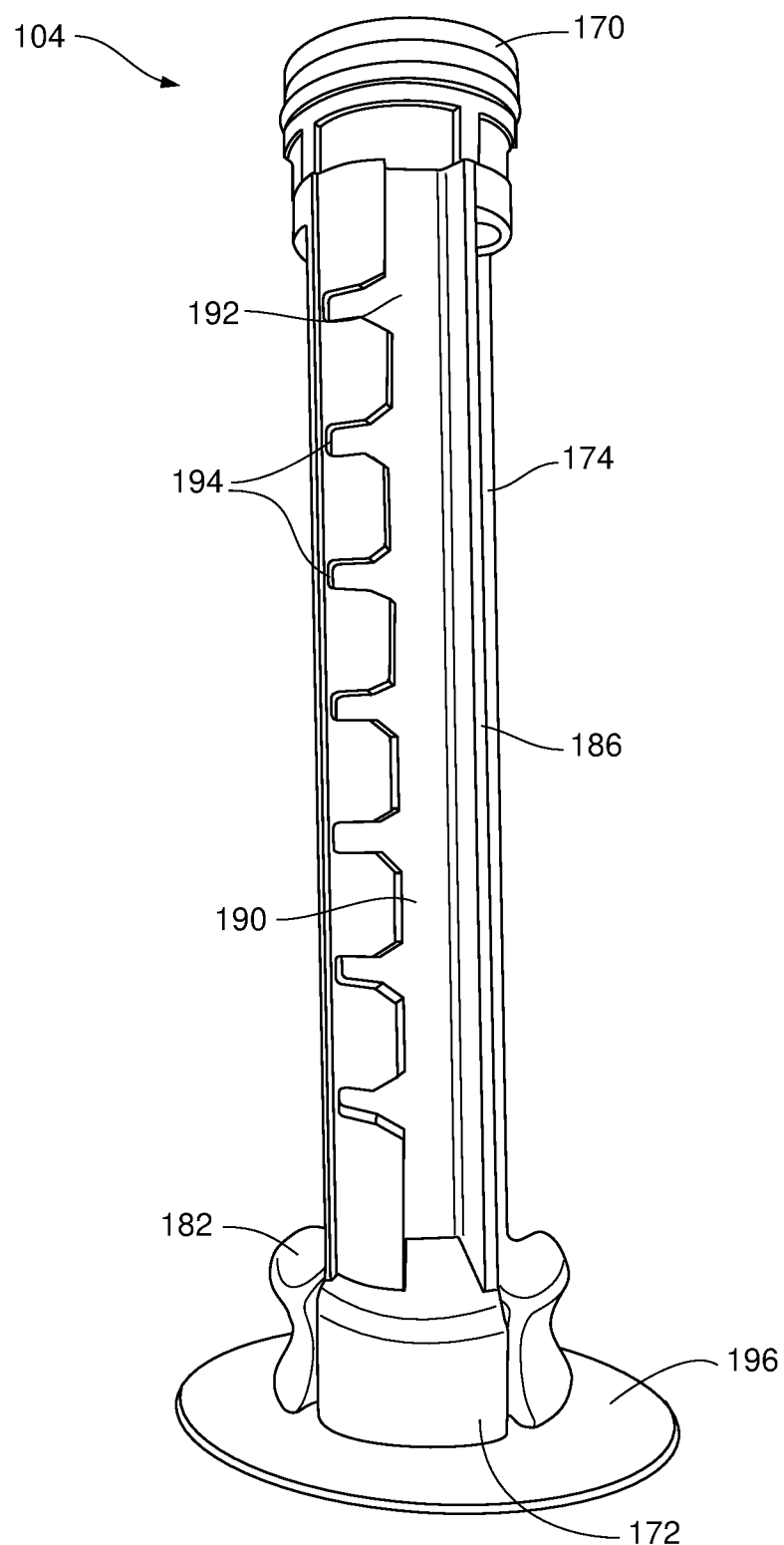
FIG. 10 is a side view of a plunger assembly of the fat harvesting system of FIG. 1 with a sizing assembly in a retracted position.
Figure 11:
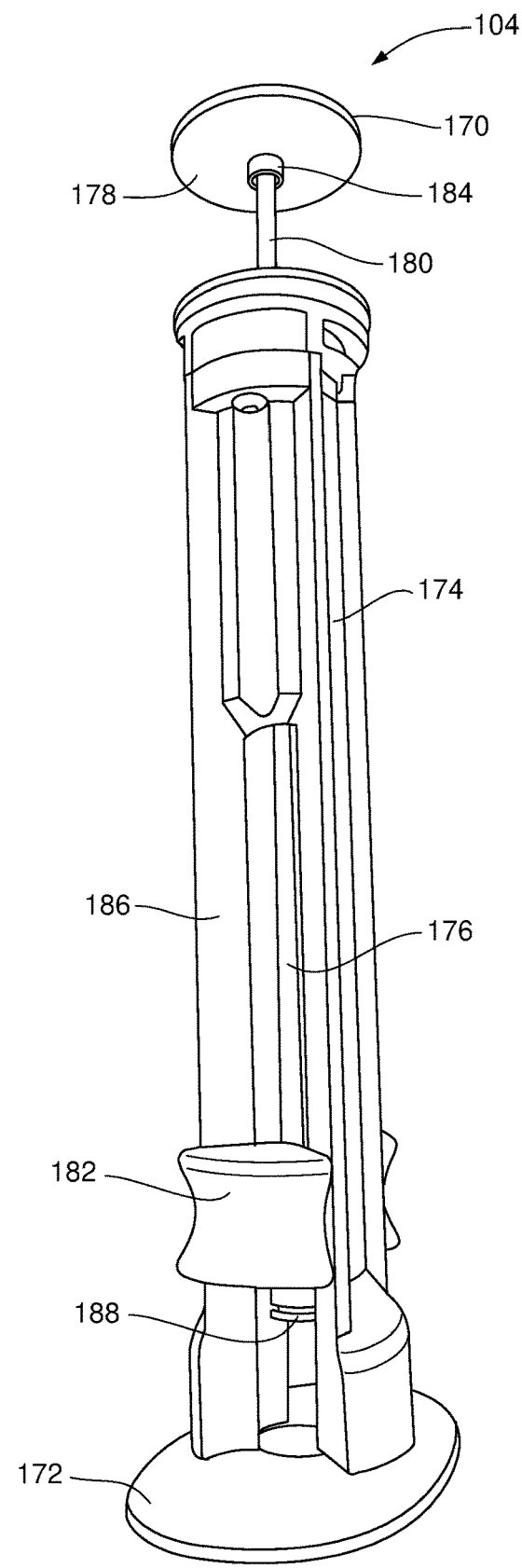
FIG. 11 is a side view of the plunger assembly of FIG. 11 with the sizing assembly in an extended position.
Figure 12:
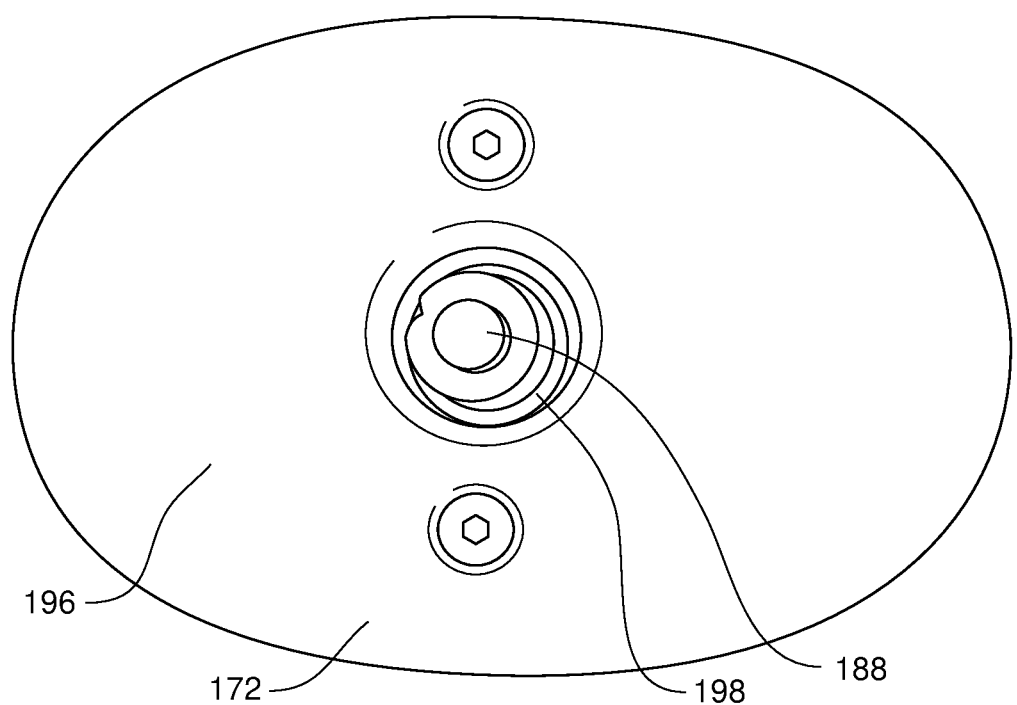
FIG. 12 is an end view of the plunger assembly of FIG. 11.

As shown in FIGS. 10, 11 and 12, plunger assembly 104 generally comprises a liquid end 170 and a biasing end 172 connected by a plunger member 174. Plunger assembly 104 further comprise a sizing assembly 176 having a porous sizing membrane 178, a sizing shaft 180 and a sizing grip 182. The sizing shaft 180 is operably, slidably mounted through a liquid end aperture 184, wherein said sizing grip 182 is mounted within a pair of plunger channels 186 defined in the plunger member 174. In some embodiments the sizing shaft 180 can be hollow and include a vacuum connector 188 proximate the sizing grip 182. Plunger member 174 can further comprise a locking channel 190 defined by a vertical channel 192 and a plurality of spaced apart horizontal channels 194. Biasing end 172 can comprise a plunger grip 196 and a biasing aperture 198 sized to accommodate the vacuum connector 188.

Generally speaking, plunger assembly 104 is slidably inserted into the cylindrical body 102 by directing the liquid end 170 into the plunger aperture 158. The locking channel 190 is positioned relative to the locking member 152 such that the locking post 156 resides within the vertical channel 192. The plunger assembly 104 can be advanced into the cylindrical body 102 such that the liquid end 170 approaches the floor cap 121.

Figure 13:
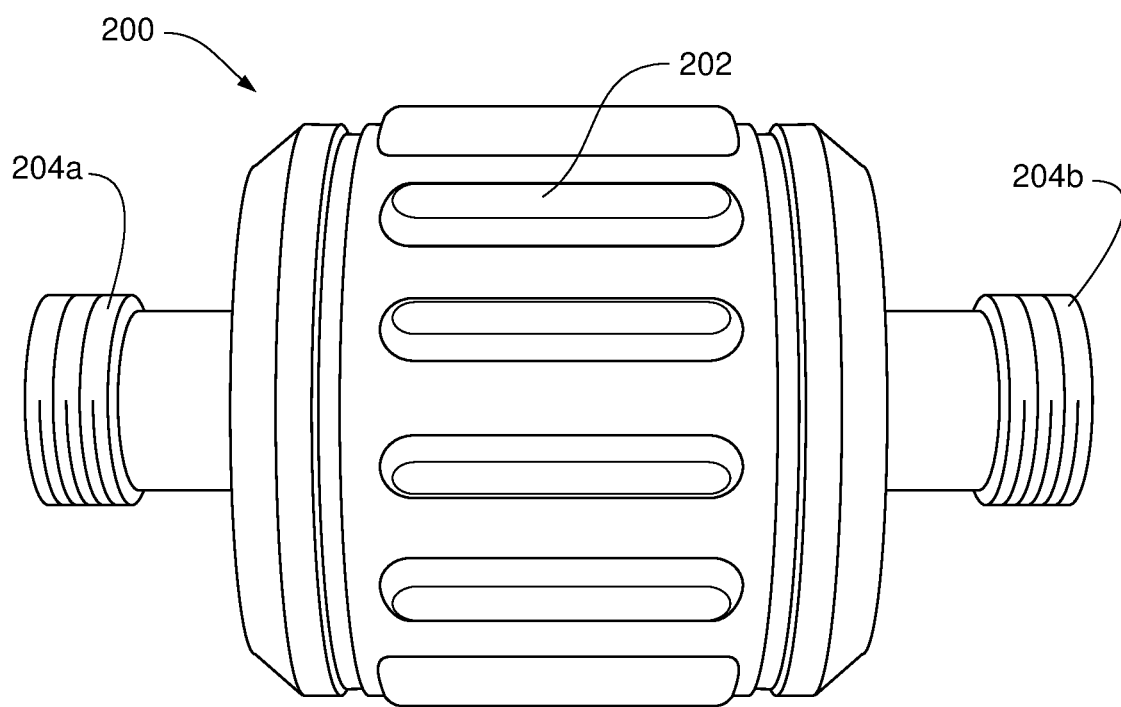
FIG. 13 is a side view of a nanofilter member for use with the fat harvesting system of FIG. 1

Depending upon the desired reinjection location of the harvested fat, it can be desirable to further reduce the size of fat particles with a nanofilter member 200 as seen in FIG. 13. Generally, nanofilter member 200 can defined a filter body 202 enclosing a permeable nanofiltration membrane (not shown) and a pair of connectors 204a, 204b such as, for example, luer connectors, at opposed ends of the filter body 202.

Figure 14:
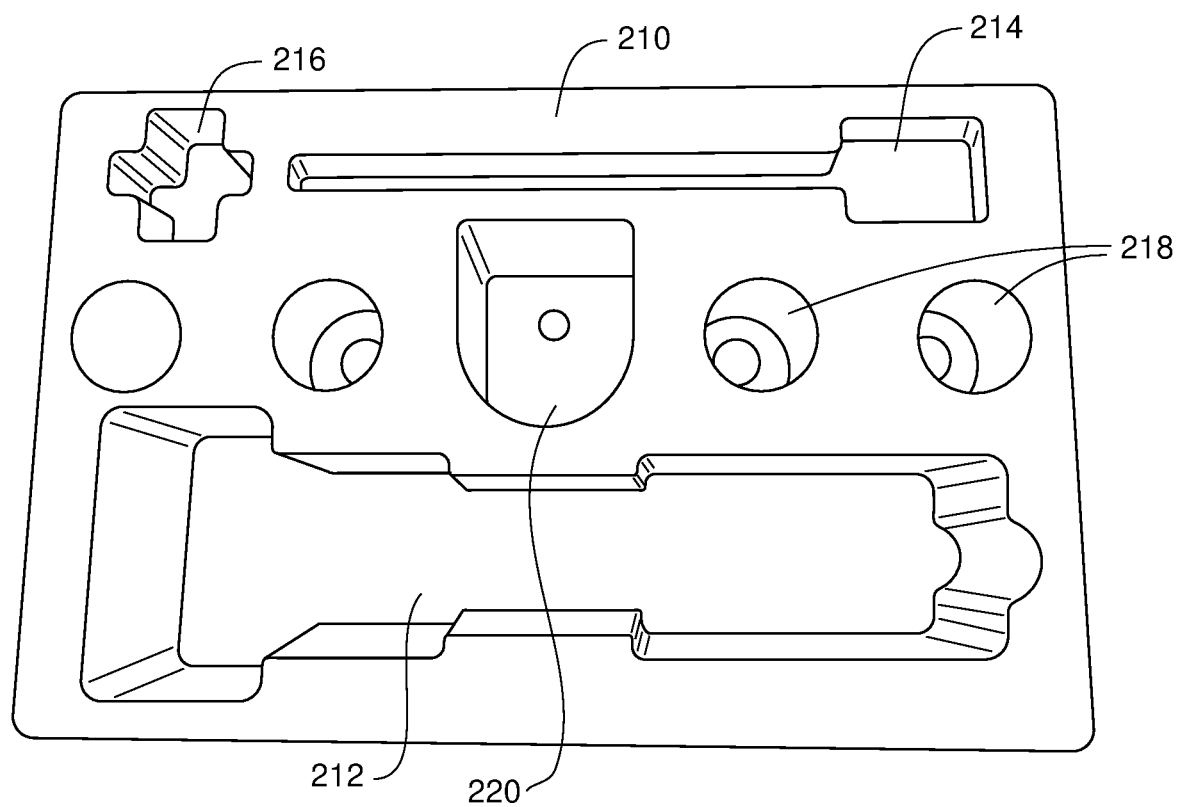
FIG. 14 is a top view of a stand for use with the fat harvesting system of FIG. 1.

Prior to use, the fat harvesting system 100 is generally packaged and shipped as a kit with a stand 210 as shown in FIG. 14. Generally, stand 210 defines a number of cavities for receiving and retaining components during shipments.

Figure 15:
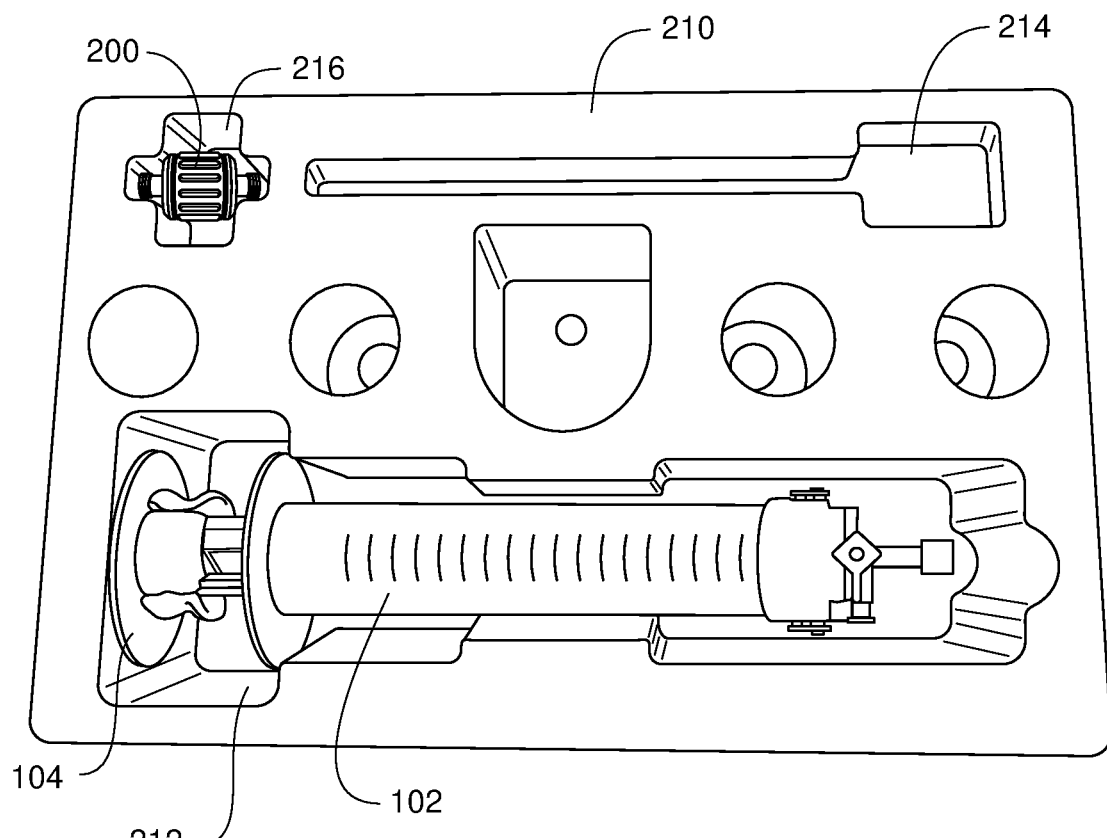
FIG. 15 is a top view of the stand retaining components of the fat harvesting system of FIG. 1 for shipment.

These cavities can include a cylindrical plunger cavity 212 for receiving the cylindrical body 102 and plunger assembly 104, a cannula cavity 214 for receiving the harvesting cannula 106 and a filter cavity 216 for receiving the nano-filter member 200 as shown in FIG. 15. Stand 210 can further include one or more syringe cavities 218 and a decanting cavity 220 as will described in further detail below.

In use, the fat harvesting system 100 generally allows a medical professional to harvest and transfer fat cells with a self-contained assembly such that procedures can be performed either a medical office environment or alternatively, in an operating room. In locations where a suction source is available, the medical professional can connect the fat harvesting system 100 to the vacuum source if so desired when harvesting and sizing fat cells. With the fat harvesting system 100, the medical professional has the ability to size fat cells based upon where they will be reinjected. Finally, as a self-contained system, the fat harvesting system 100 is a single use, disposable assembly requiring no sterilization equipment.

Generally, a method for harvesting fat cells commences by attaching the harvesting cannula 106 to the cylindrical body 102 using the connector 110 and conduit connector 126a as shown in FIGS. 1 and 2. The user then rotates the manual valve member 134 such that the first conduit 126 is open to fluid communication with the body interior and the second conduit 128 is closed off. The user then positions the needle tip 112 proximate a fat harvesting location such as the outer thigh and then inserts the needle tip 112 into the fat harvesting location. While gripping the cylindrical body 102, the user can then pull on the plunger grip 196 to begin withdrawing the plunger assembly 104 the cylindrical body 102, thereby inducing a vacuum condition within the body interior 132 which is communicated through the first conduit 126 and ultimately to the needle tip 112. With a vacuum condition at needle tip 112, fat cells are suctioned through the harvesting cannula 106, into the first conduit 126 and ultimately into the body interior 132 where the user can compare the amount of fat cells recovered to the volumetric indicia 148. The medical professional can move the needle tip 112 within the fat harvesting location while continuing to withdraw the plunger assembly 104 until a desired volume of fat cells is recovered. Depending upon the reinjection location, it may be desirable to size the cylindrical body 102 to have a desired maximum volume for the body interior 132, for example, 20 ml or 100 ml. Once the desired volume of fat cells has been recovered, the user can turn the manual valve member 134 such that the body interior 132 is closed off from the first conduit 126 and the second conduit 128 is in fluid communication with the body interior 132. The user can then advance the plunger assembly 104 back into the cylindrical body 102 to vent any accumulated air within the body interior 132 out the second conduit 128. With the air vented from the body interior 132, the user can turn the manual valve member 134 such that the body interior 132 is closed off from the first conduit 126 and second conduit 128 so as to avoid loss of the recovered fat cells. The user can then detach the harvesting cannula 106 from the first conduit 126 and appropriately dispose of the harvesting cannula 106.

In the event that the fat harvesting system 100 is utilized in an operating room with an available vacuum source, the step of withdrawing the plunger assembly 104 to induce a suction condition within the cylindrical body 102 can alternatively be replaced with connecting the available vacuum source to the vacuum connector 188 on the sizing assembly 176. When utilizing the vacuum source, the user would simply slide the plunger assembly 104 to create a desired open volume with the body interior 132 and utilize the vacuum source to draw fat cells through the harvesting cannula 106 until the desired volume of fat cells is harvested. At that point, the user could remove the vacuum source and the recovery and sizing procedure could otherwise proceed.

Figure 16:
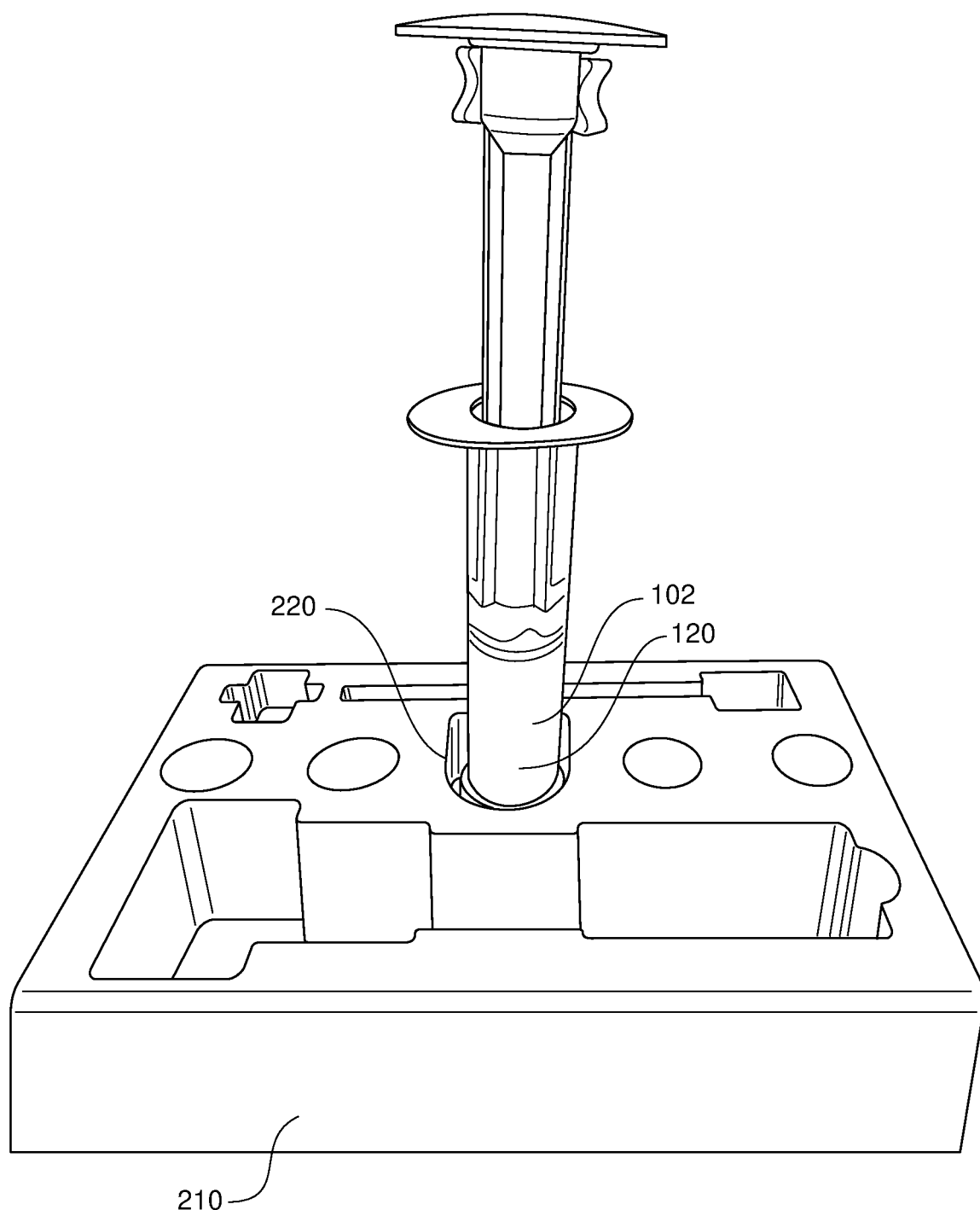
FIG. 16 is a side view of the stand retaining the fat harvesting system of FIG. 1 during a decanting step.

Following harvesting of the fat cells, the rotatable cover 106 can be rotated to an open position so as to allow flow through the porous floor screen 140. The user can then position the cylindrical body 102 such that the treatment end 120 is placed into the decanting cavity 220 and the cylindrical body 102 is held in a vertical position as shown in FIG. 16. With the cylindrical body 102 in the vertical position, the harvested fat cells within the body interior 132 will then begin to separate and form distinct layers based upon the specific gravity of the various biological components. For example, an oil layer including the recovered fat cells and free lipids are generally less dense than a water layer such that the oil layer will generally form above the water layer with the cylindrical body 102 in the vertical position. Generally, the oil/water interface is easily visible and once separated, a user can advance the plunger assembly 104 into the cylindrical body 102 such that water layer is evacuated through the porous floor screen 140. Once the water layer has been evacuated from the body interior 132, the user rotates the rotatable cover 106 to a closed positon to prevent further loss through the porous floor screen 140.

With the water layer removed from the body interior 132, the user can then begin sizing the recovered fat cells. Generally, the user locks the position of the plunger assembly 104 relative to the cylindrical body 102 by rotating the plunger member 174 such that the locking post 156 slides into one of the horizontal channels 194. With the locking post 156 retained within one of the horizontal channels 194, the plunger member 174 is prevented from being inserted or withdrawn relative to the cylindrical body 102. With the positon of the plunger member 174 fixed relative to the cylindrical body 102, the user can grasp the sizing grip 182 and slide the sizing grip 182 along the plunger channels 186 and toward the treatment end 120. Movement of the sizing grip 182 toward the treatment end 120 directs the sizing shaft 180 and consequently the porous sizing membrane 178 through the recovered fat cells in the body interior 132. As the porous sizing member 178 is directed toward the floor cap 121, the recovered fat cells are forced through the porous sizing member 178 such that they are broken down into smaller sizes capable of passing through the porous sizing member 178. In one preferred embodiment, the porous sizing member 178 can include pores with a diameter of 1.5 mm for sizing fat cells suitable for reinjection into breast tissue. Using the sizing grip 182, the sizing assembly 176 and porous sizing member 178 specifically can be directed back and forth through the recovered fat cells until the fat cells have achieved the desired size.

Figure 17:
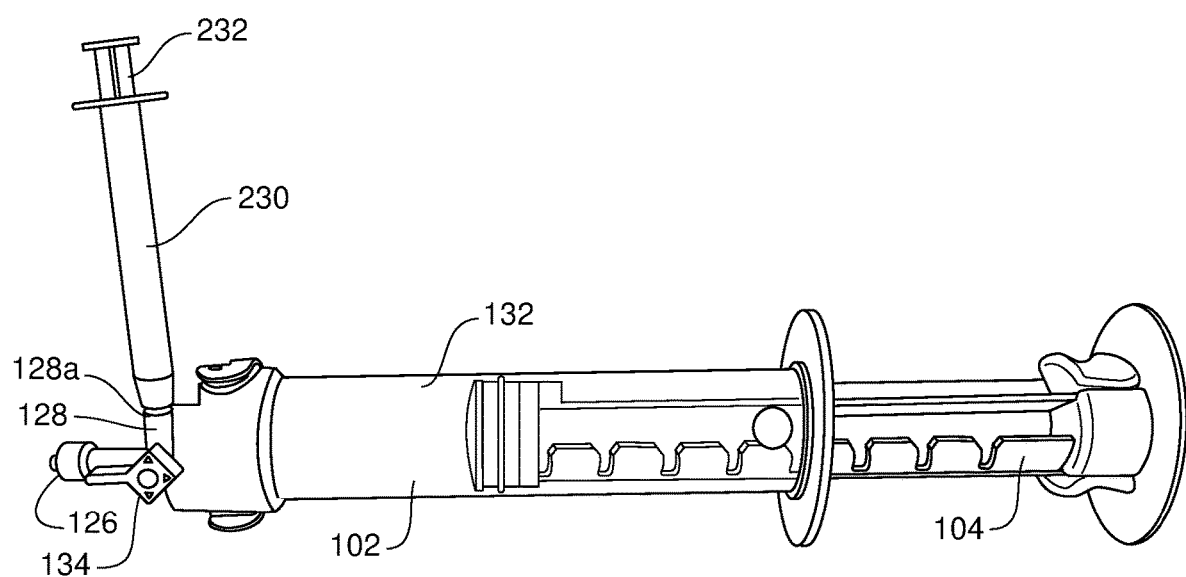
FIG. 17 is a side view of the fat harvesting system of FIG. 1 during an injecting syringe filling step through a second conduit.
Figure 18:
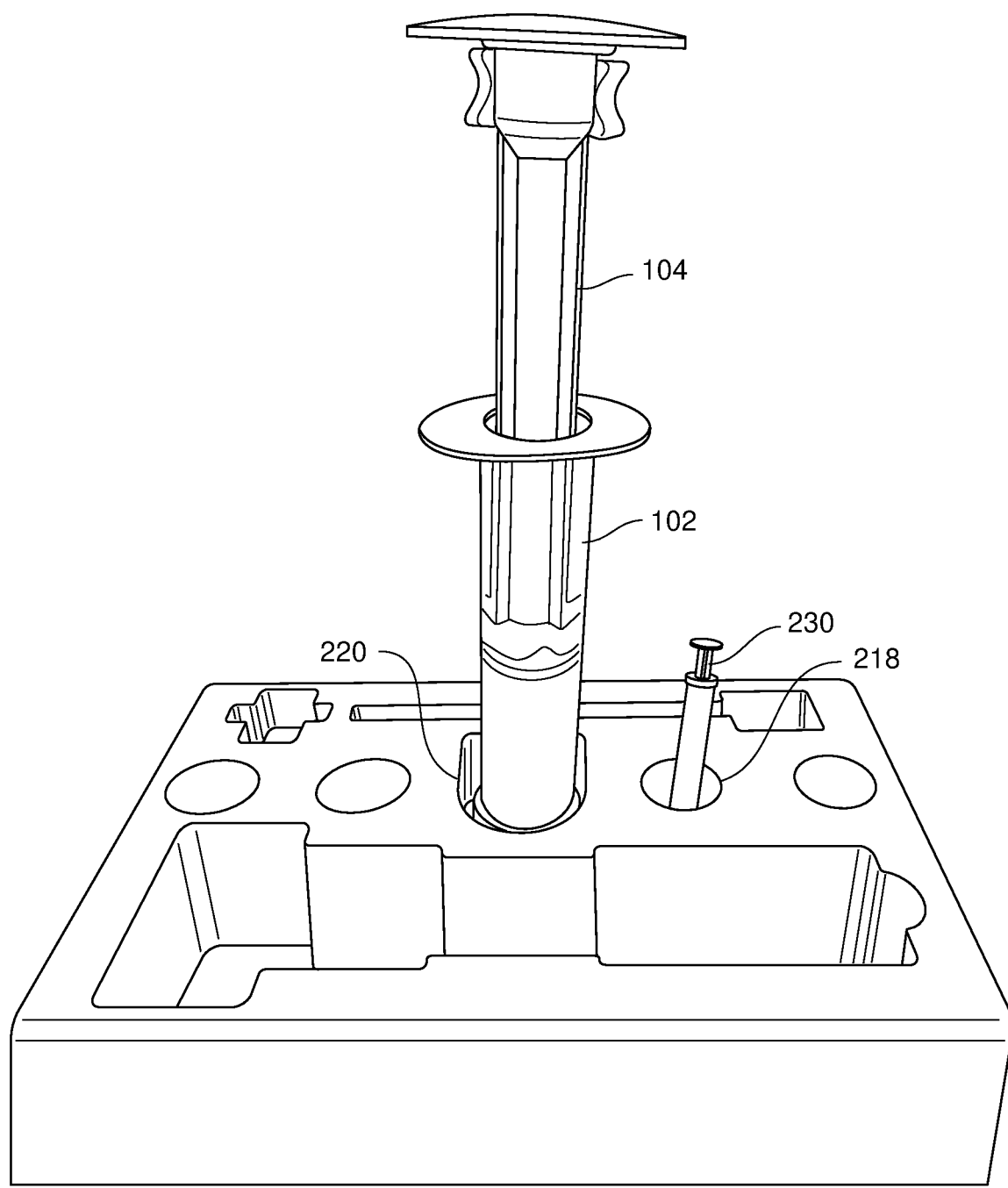
FIG. 18 is a side view of the stand of FIG. 14 retaining the fat harvesting system of FIG. 1 and a filled injection syringe.

Once the recovered fat cells have been sized with the sizing assembly 176, a user can attach an injection syringe 230 to the conduit connector 128a of the second conduit 128 as seen in FIG. 17. The manual valve 134 can then be rotated to fluidly connect the second conduit 128 with the body interior 132 while closing off the first conduit 126. By simultaneously withdrawing a syringe plunger 232 as the plunger assembly 104 is advanced into the cylindrical body 102, the sized fat cells can be transferred from the body interior 132 to the injection syringe 230. Once filled, the injection syringe 230 can be placed in one of the syringe cavities 218 as shown in FIG. 18 and the process can be repeated to fill additional injection syringes 230. Using the filled injection syringes 230, the user can transfer and inject the sized fat cells into the desired body location.

Figure 19:
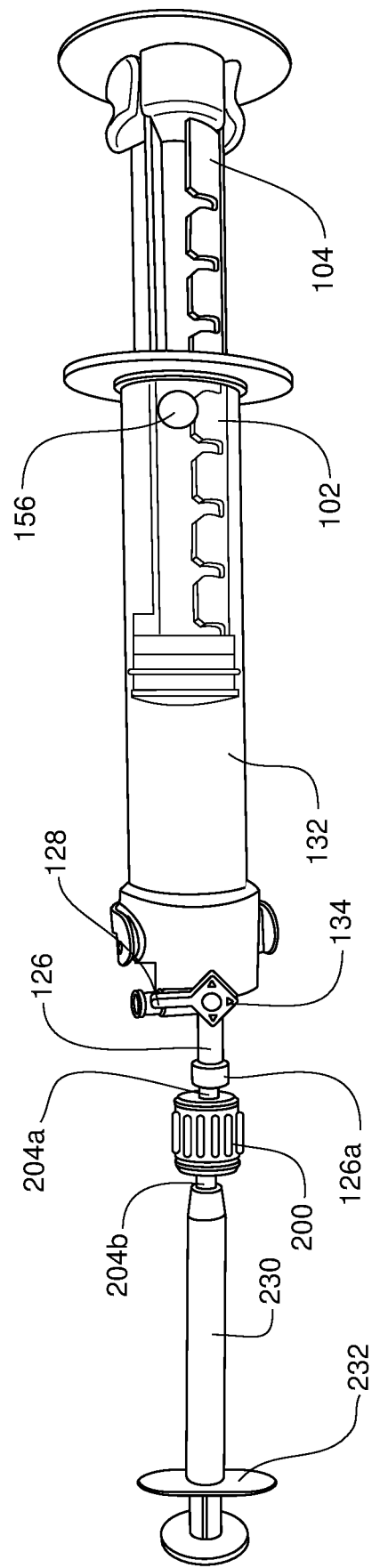
FIG. 19 is a side view of the fat harvesting system of FIG. 1 during a nonfilter sizing step through a first conduit.
Figure 20A:
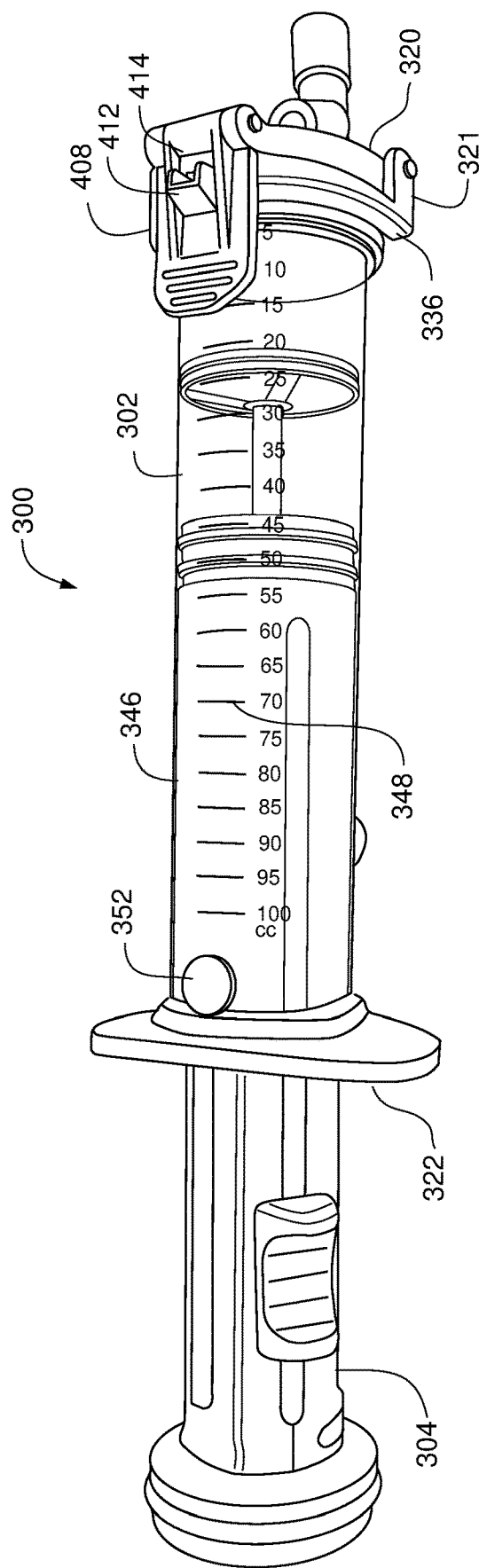
FIG. 20A is side view of a fat harvesting system according to another representative embodiment of the invention.
Figure 20B:
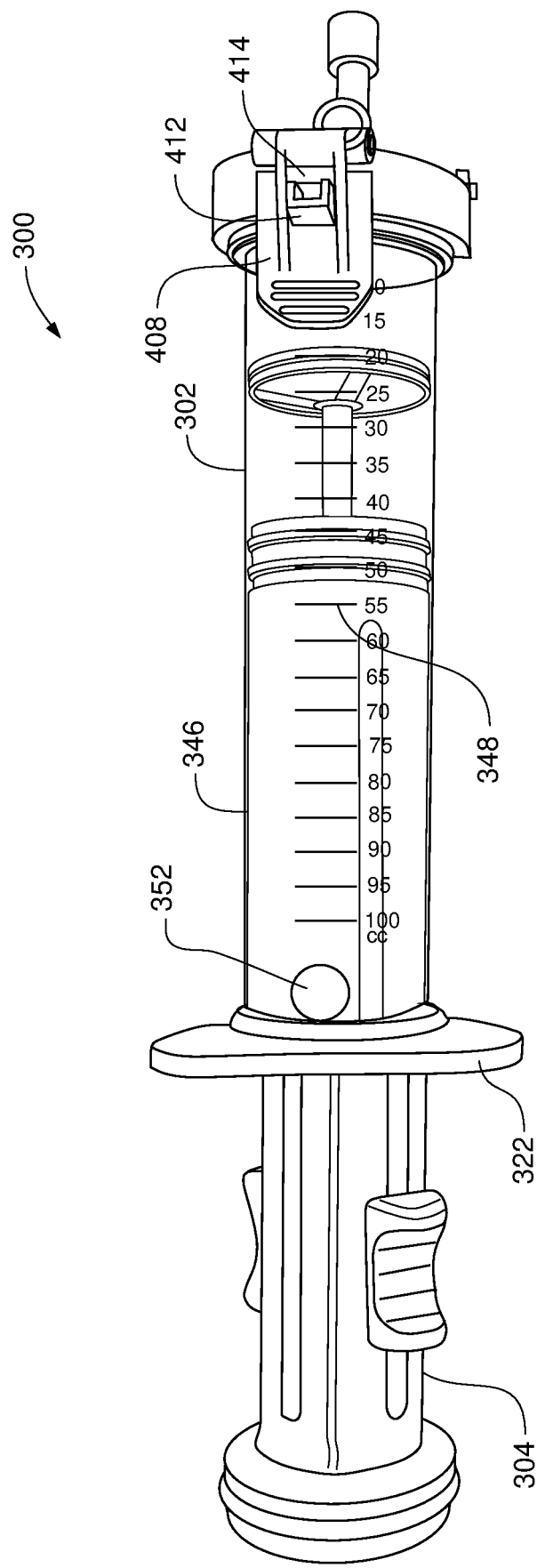
FIG. 20B is a side view of the fat harvesting system of FIG. 20A
Figure 20C:
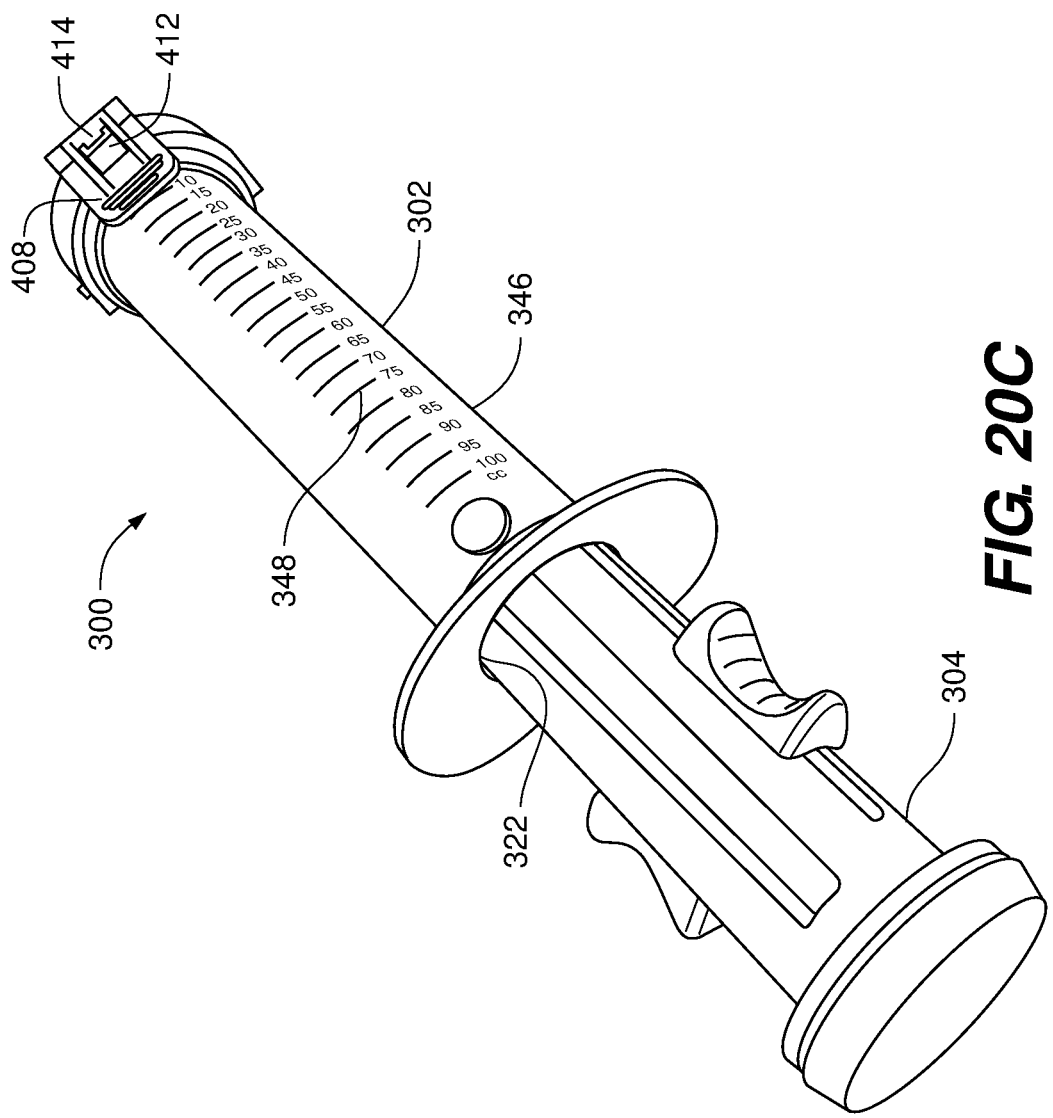
FIG. 20C is a perspective, end view of the fat harvesting system of FIG. 20A.
Figure 20D:
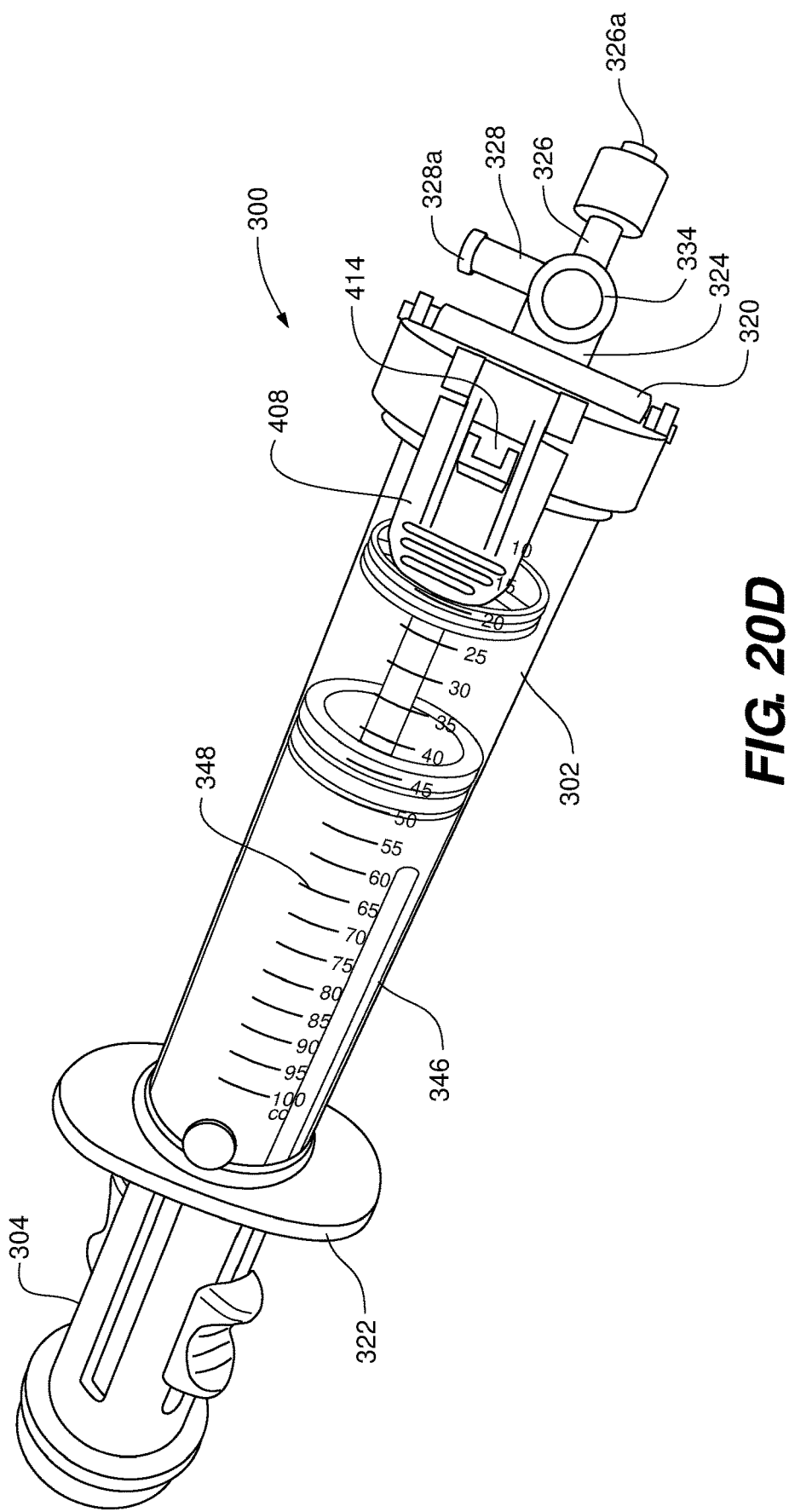
FIG. 20D is a perspective, end view of the fat harvesting system of FIG. 20A.
Figure 21A:
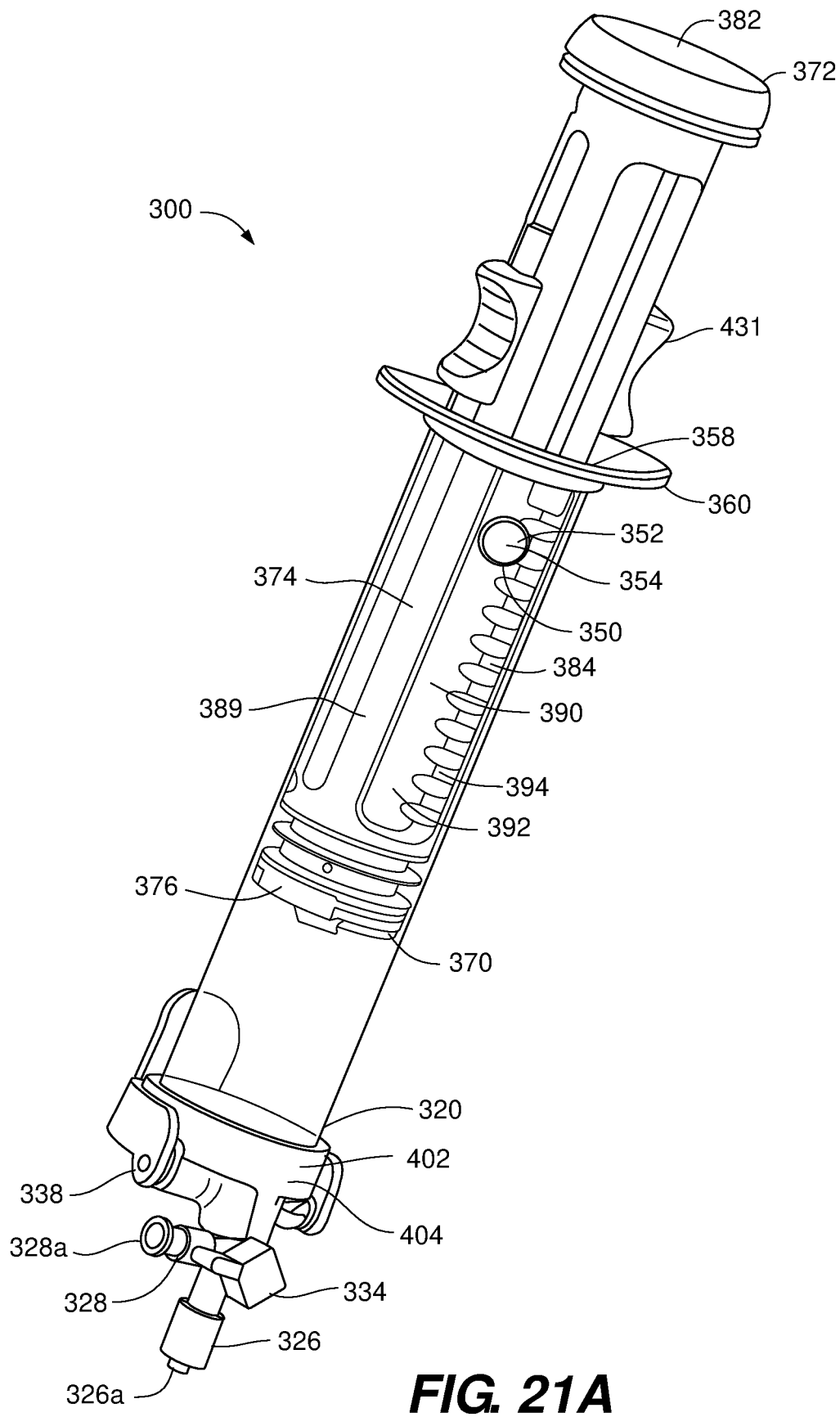
FIG. 21A is a perspective view of the fat harvesting system of FIG. 20A.
Figure 21B:
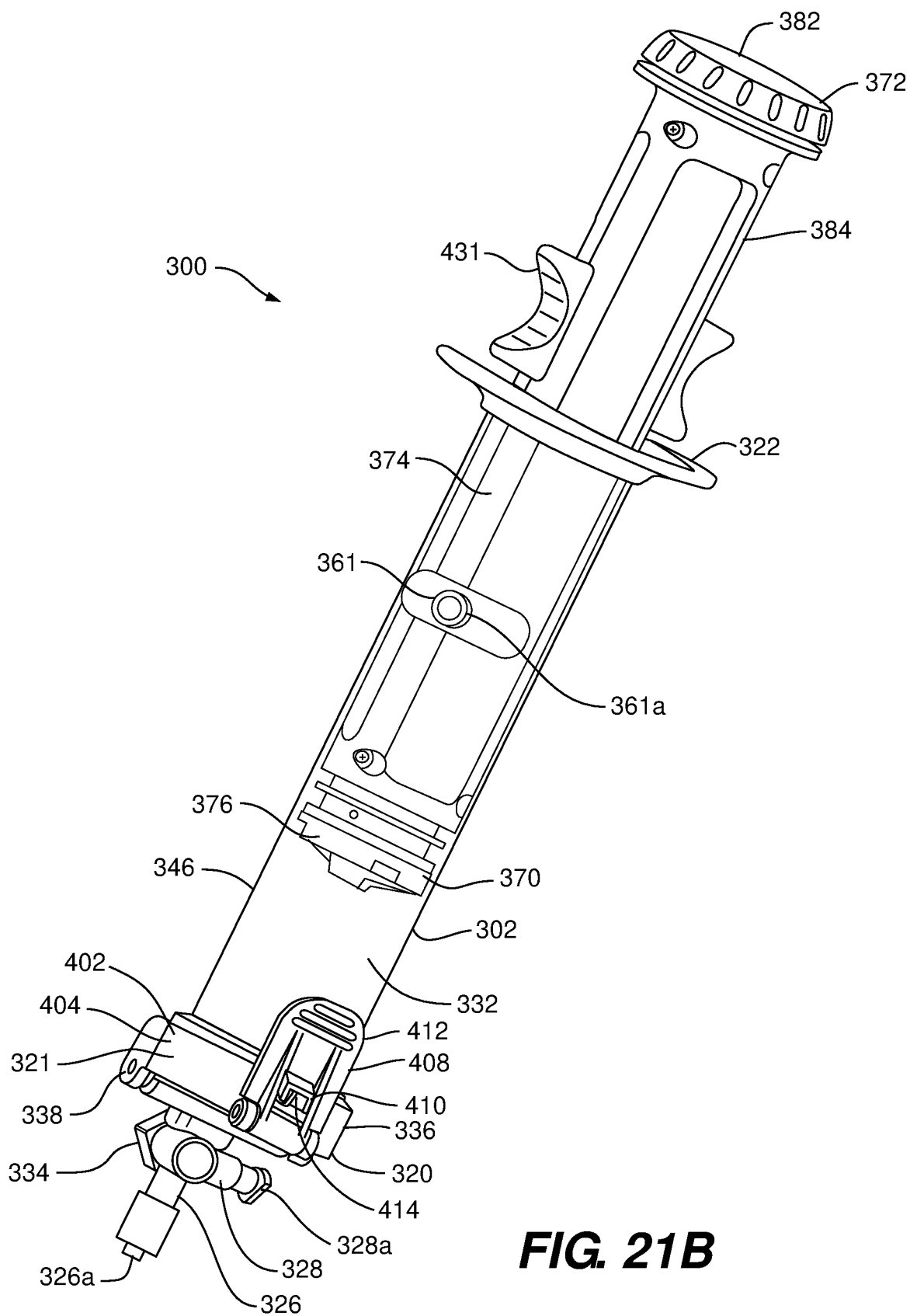
FIG. 21B is a perspective view of the fat harvesting system of FIG. 20A.
Figure 22:
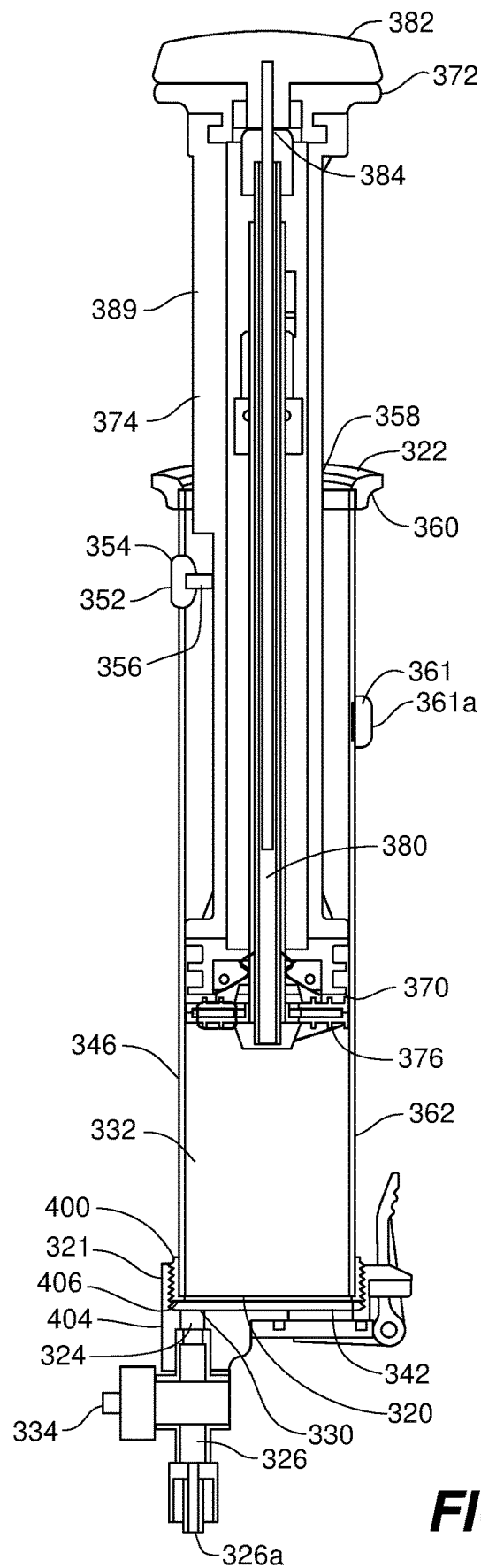
FIG. 22 is a side, section view of the fat harvesting system of FIG. 20A.

For locations requiring even smaller sized fat cells, the user can attach the nanofilter member 200 to the conduit connector 126a of the first conduit 126 using connector 204a as shown in FIG. 19. Next, a user can attach injection syringe 230 to connector 204b. The manual valve 134 can be rotated to fluidly connect the first conduit 126 to the body interior 132 while closing off the second conduit 128. By simultaneously withdrawing the syringe plunger 232 as the plunger assembly 104 is advanced into the cylindrical body 102, the sized fat cells can be transferred from the body interior 132, through the nanofilter member 200 and into the injection syringe 230. As the sized fat cells pass through the nanofilter member 200, the sized fat cells are forced through even smaller pores in the permeable nanofiltration membrane which will generally have a pore diameter less than 1.5 mm. In a manner similar to that previously described with respect to porous sizing member 178, the sized fat cell can be passed back and forth through the nanofilter member 200 such that the fat cells are continually broken down into smaller sizes. The user can then fill the injection syringe 230 with nanosized fat cells and place the syringe 230 in one of the syringe cavities 218 and additional syringes 230 can now be filled.

Referring now to FIGS. 20A-32, another representative embodiment of a fat harvesting system 300 is illustrated. Generally, fat harvesting system 300 can be utilized as a self-contained fat harvesting and transfer system in much the same way as fat harvesting system 100. Similar to fat harvesting system 100, fat harvesting system 300 provides a medical professional with flexibility to use the system in a traditional surgical suite with a readily available vacuum source or alternatively, in a non-traditional surgical setting where the fat harvesting system 300 functions as its own source of vacuum. In addition, fat harvesting system 300 similarly provides professional flexibility with respect to how the medical professional chooses to perform certain fat recovery and processing steps such as, for example, a speed by which the various fat components are separated and the sizing of fat cells for reinjection. While the medical professional may choose to utilize available surgical resources such as, for example, a vacuum source with the fat harvesting system 300, the fat harvesting system 300 is otherwise capable of harvesting, processing and transferring fat cell s without the use of additional external inputs.

Generally, fat harvesting system 300 as shown in FIGS. 20A, 20B, 20C, 20D, 21A and 21B can comprise a cylindrical body 302 and a plunger assembly 304 that is utilized in conjunction with the harvesting cannula 106. As discussed previously, it may be that the medical professional utilizes a powered liposuction device in place of the harvesting cannula 106 based on personal preference and availability. Fat harvesting system 300 is similarly designed to fat harvesting system 100 with respect to material of construction and is intended as a single procedure system such that no additional sterilization techniques or procedures are necessary. In addition, cylindrical body 302 can be sized to have a variety of different volumetric capacities based on the procedure and volume of fat cells to be recovered, for example, 100 cc, 500 cc or 1000 cc, without departing from the basic design and operation of the fat harvesting system 300.

Figure 23:
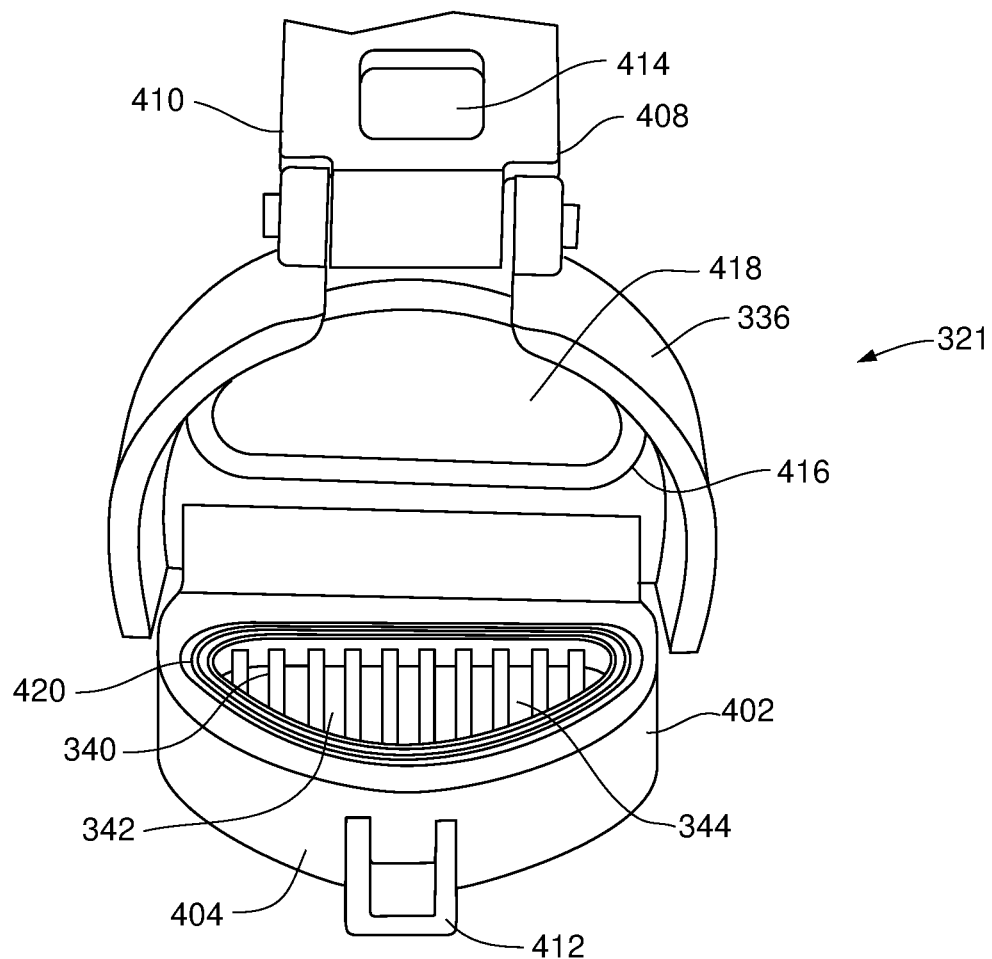
FIG. 23 is a perspective view of an end cap for use with the fat harvesting system of FIG.
Figure 24:
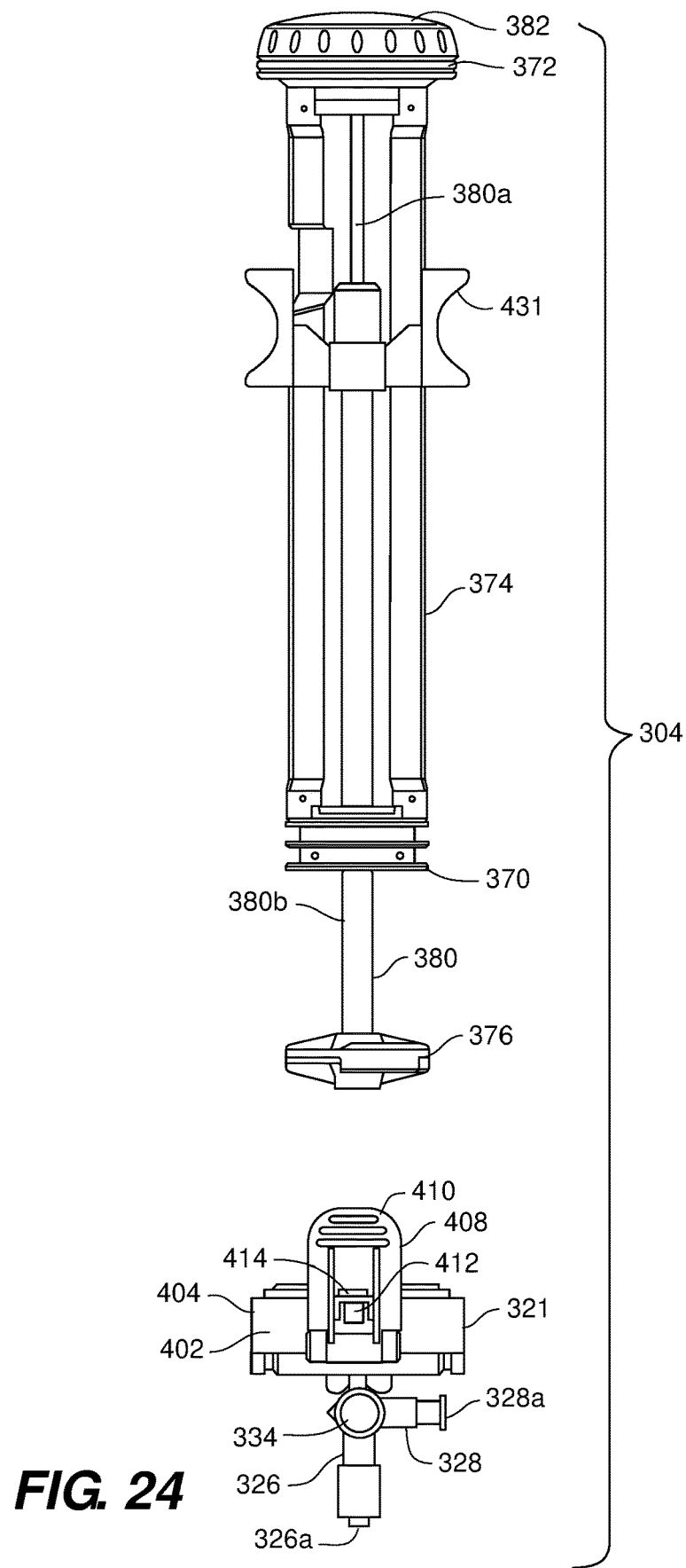
FIG. 24 is a side view of a plunger assembly and end cap for use with the fat harvesting system of FIG. 20A.
Figure 25:
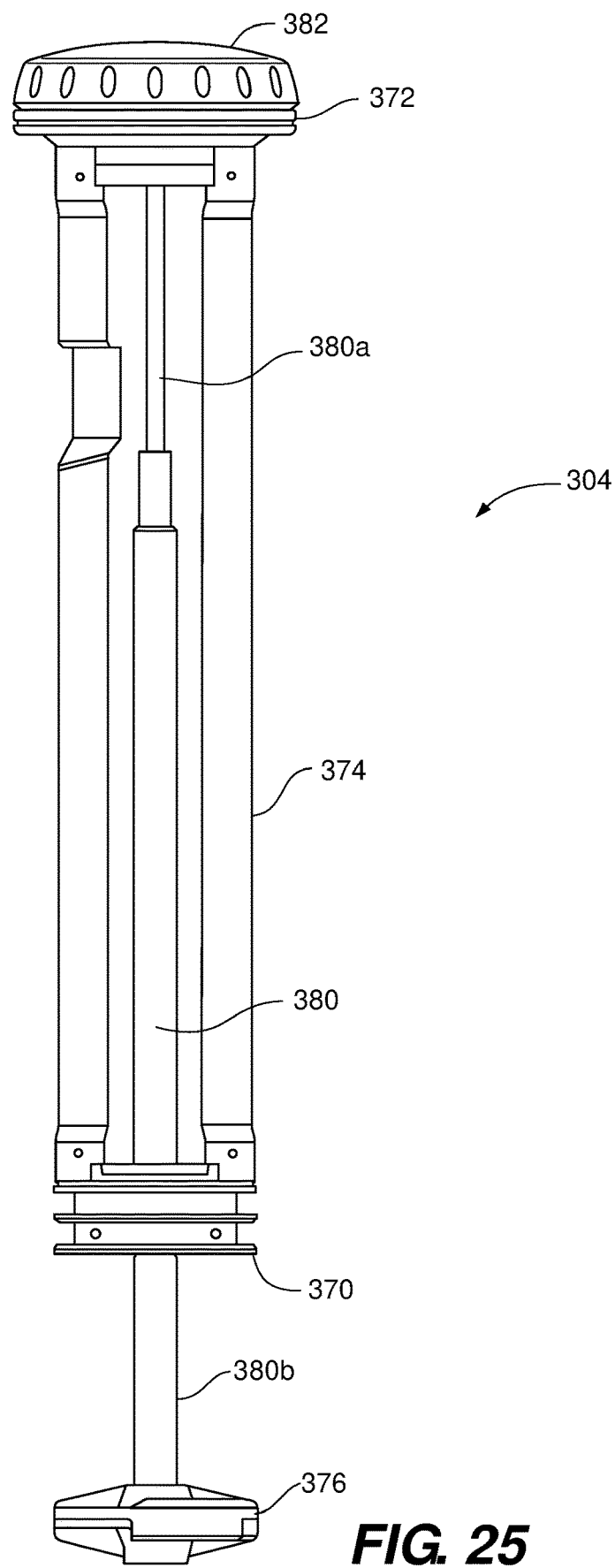
FIG. 25 is a side view of a plunger assembly for use with the fat harvesting system of FIG. 20A.
Figure 26:
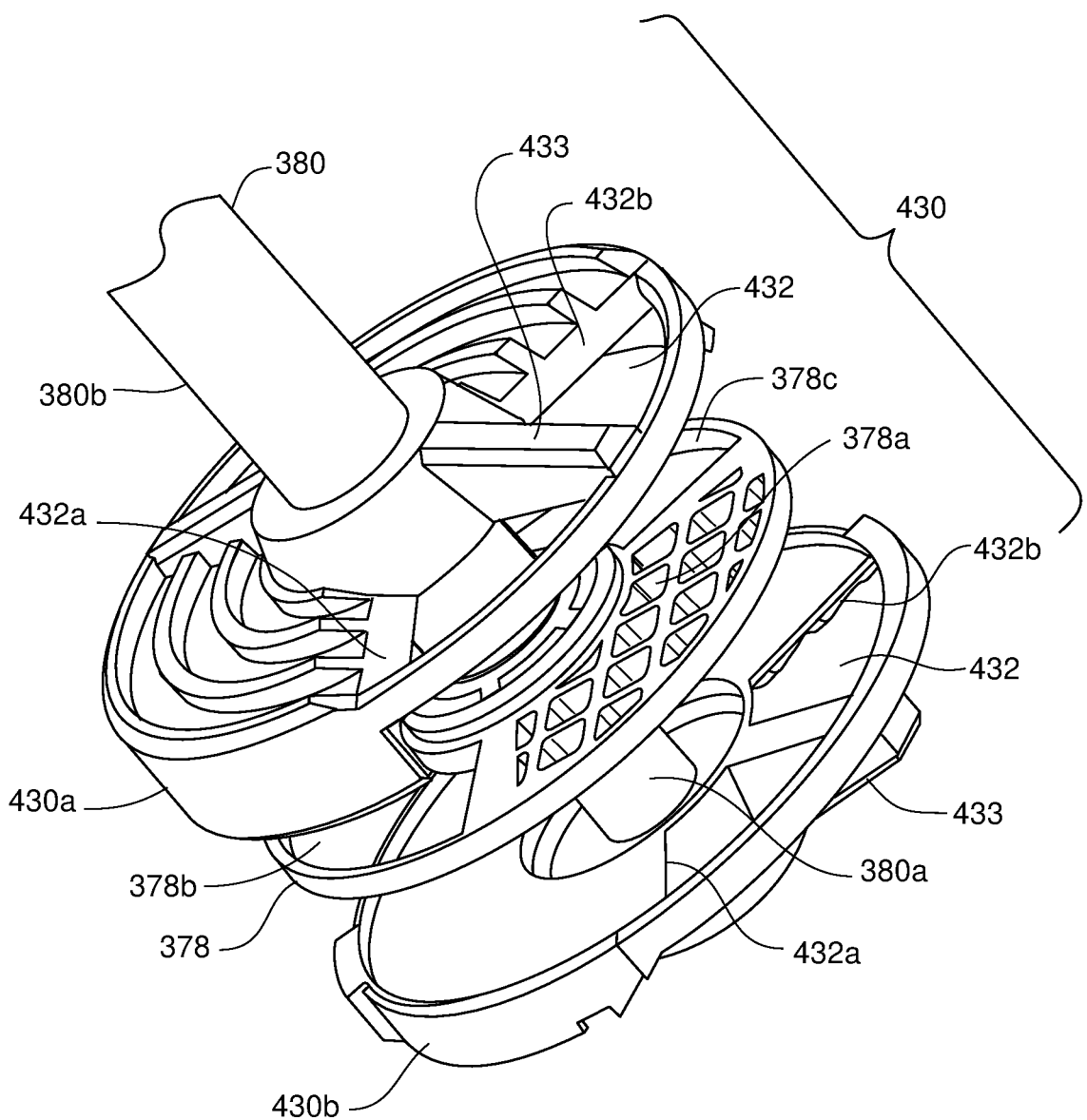
FIG. 26 is an exploded, perspective view of a sizing assembly for use with the fat harvesting system of FIG. 20A.
Figure 27:
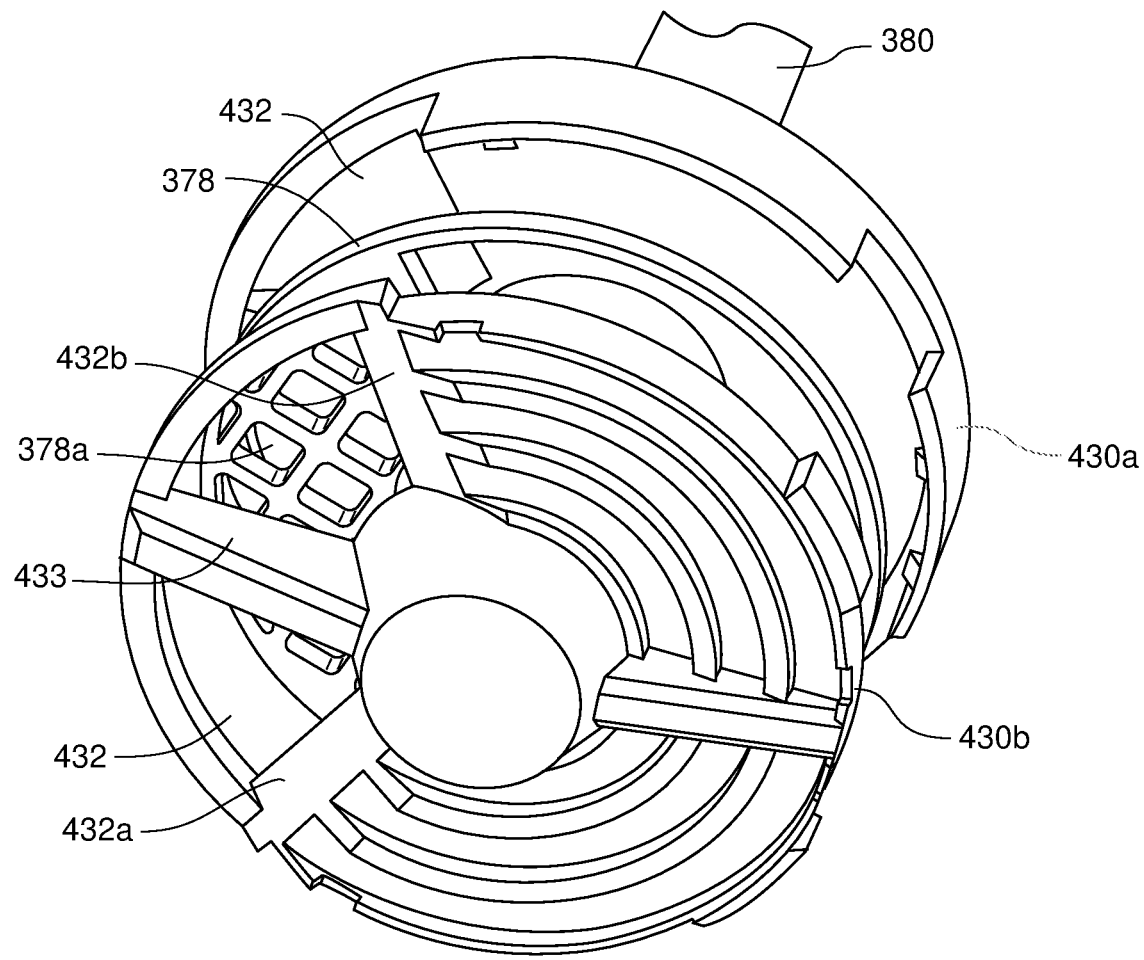
FIG. 27 is an exploded, perspective end view of the sizing assembly of FIG. 26.
Figure 28:
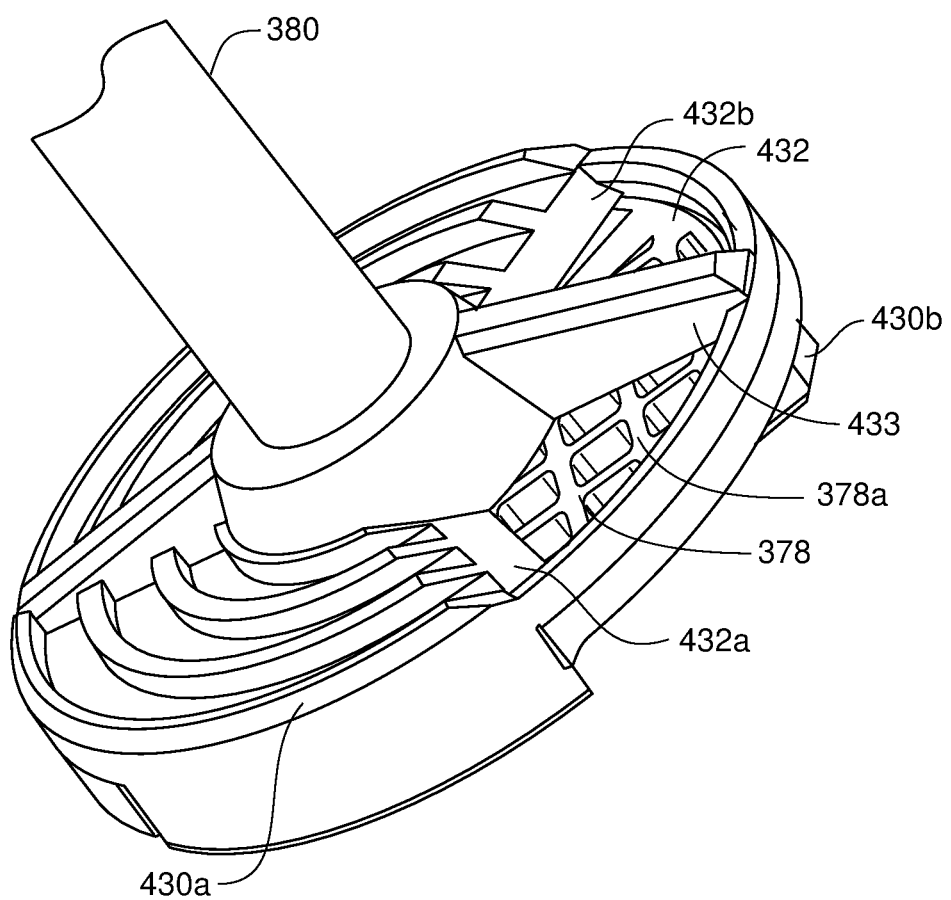
FIG. 28 is a perspective view of the sizing assembly of FIG. 26.
Figure 29:
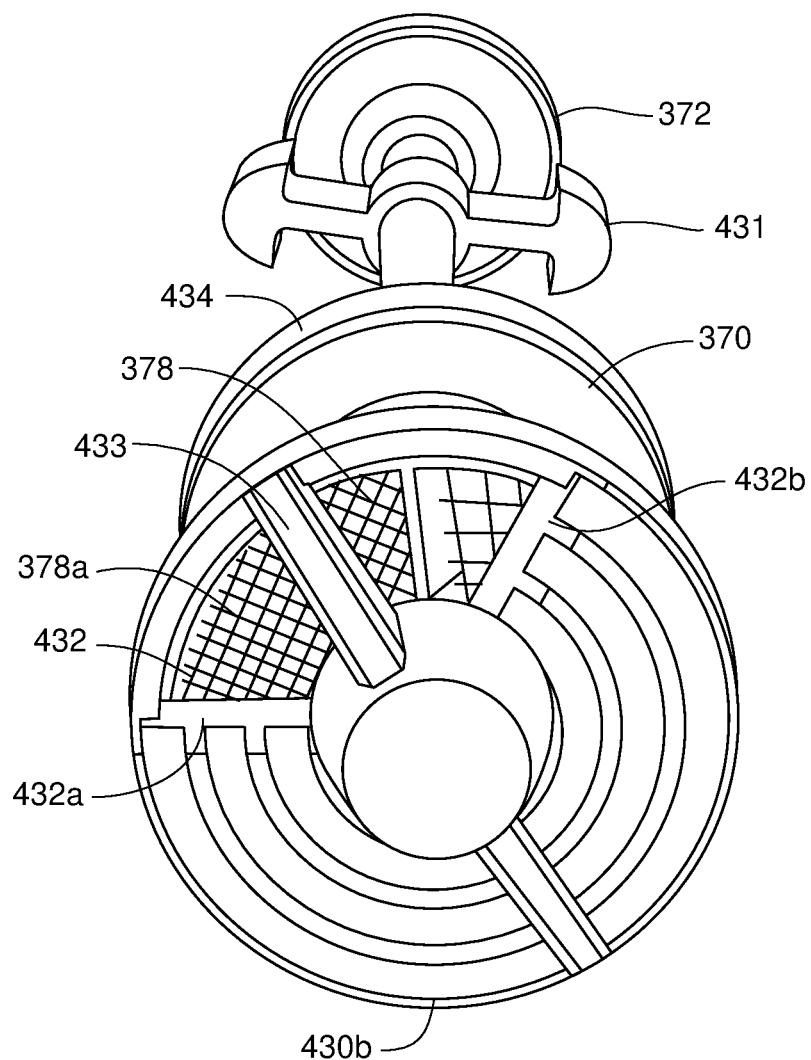
FIG. 29 is a perspective end view of the sizing assembly of FIG. 26.
Figure 32:
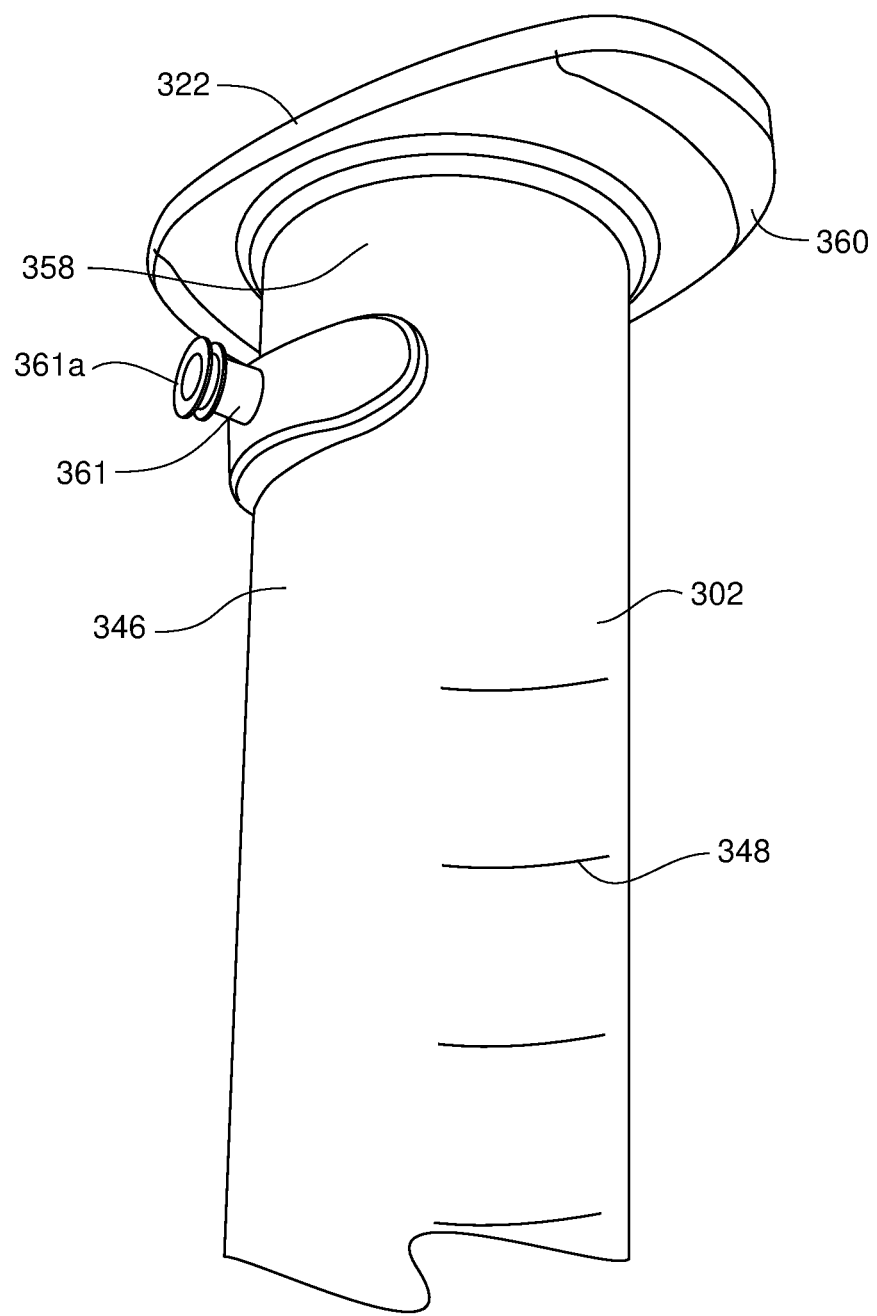
FIG. 32 is a side view of the cylindrical body of FIG. 30.

Cylindrical body 302 is generally similar in appearance and construction to cylindrical body 102 with differences found primarily at a treatment end 320. Cylindrical body 302 is generally defined between the treatment end 320 and an open end 322 as seen in FIGS. 20A-22. Treatment end 320 generally includes a floor cap 321 for closing off the treatment end 320. Floor cap 321 generally includes a flow conduit 324 including a first conduit 326, a second conduit 328, each including an associated conduit connector 326a, 328a. Flow conduit 324 is operably mounted into a cylinder floor aperture 330 defined in the floor cap 321 such that the flow conduit 324 is operably, fluidly coupled with a body interior 332. Flow conduit 324 includes a manual valve member 334 for selectively opening and closing access between the first conduit 326, the second conduit 328 and the body interior 332. As seen in FIG. 23, floor cap 321 further comprises a rotatable cover 336 rotating about a cover hinge 338 to selectively allow flow through a porous floor screen 340 covering a floor opening 342 defined in the floor cap 321. The floor opening 342 can comprise one or more screen support members 344 over which the porous floor screen 340 can be mounted and supported. As seen in FIG. 32, cylindrical body 302 generally defines a body wall 346 that can include volumetric indicia 348 and a side aperture 350 in which a locking member 352 is mounted therein. Locking member 352 can include a tab portion 354 and a locking post 356 that extends through the side aperture 350 and projects into the body interior 332. Open end 322 generally defines a plunger aperture 358 and a body grip 360. Cylindrical body 302 can further comprise a vacuum port 361 through the body wall 346 such that a port connection 361a is in fluid communication with the body interior 332.

Cylindrical body 302 generally comprises an external thread 400 proximate the treatment end 320 that allows the floor cap 321 to be selectively, rotatably attached and removed from the treatment end 320 so as to expose the body interior 332 at the discretion of the medial professional. Floor cap 321 includes a cap body 402 defined by a circumferential cap wall 404 that is generally sized so as to rotatably receive the treatment end 320. Circumferential cap wall 404 includes an internal thread 406 that can rotatably engage the external thread 400.

Floor cap 321 further comprises a latch assembly 408 that allows for positive retention of the rotatable cover 336 in a closed position. Latch assembly 408 generally includes a latch tab 410 on the rotatable cover 136 and a latch member 412 that is located on the circumferential cap wall 404. The latch tab 410 can define a latch opening 414 that can be snapped over the latch member 412 such that the rotatable cover 336 is physically retained in the closed position, which is especially advantageous when pressure is applied within the body interior 332 such that a non-intentional opening of rotatable cover 336, which could ruin or waste harvested fat cells. When the medical professional decides to open the rotatable cover 336 to expose the porous floor screen 340 and floor opening 342, the latch tab 410 is simply pulled away from latch member 412 and the rotatable cover 336 is allowed to rotate to an open position. Floor cap 321 can further comprise a floor seal 416 on an inner surface 418 of the floor cap 321, wherein said floor seal 416 is sized and shaped to seat within a sealing groove 420 that surrounds the floor opening 342. When the latch tab 410 is physically engaged with the latch member 412, the floor seal 416 is compressed within the sealing groove 420 to prevent leakage through the floor opening 342 when the rotatable cover 336 is in the closed position.

As shown in FIGS. 20A-22, 24 and 25, plunger assembly 304 generally comprises a liquid end 370 and a biasing end 372 connected by a plunger member 374. Plunger assembly 304 further comprises a sizing assembly 376 having a porous sizing screen 378, a sizing disc assembly 430, a sizing shaft assembly 380, a sizing shaft grip 431 and a sizing selector 382 as shown in FIGS. 26-31. Porous sizing screen 378 generally comprises a flat, disc shaped screen that can comprise a plurality of screen portions, for example, screen portions 378a, 378b, 378c, wherein each of the screen portions has a different size pore or screen opening. For instance, screen portion 378a could have screen openings of 2.4 mm, screen portion 378b could have screen openings of 1.2 mm and screen portion 378c could have screen openings of 0.6 mm. The sizing disc assembly 430 generally comprises a pair of sizing discs 430a, 430b that are located on each side of the porous sizing screen 378. Generally, each sizing disc 430a, 430b generally defines a sizing window 432, wherein the size of the sizing window 432 is generally dictated by the number of screen portions in the porous sizing screen 378. For example, the sizing window 432 generally defines a 120° arcuate portion of each sizing disc 430a, 430b when there are three screen portions 378a, 378b, 378c (360°/3 screen portion equals 120° arcuate portion). Similarly, if there were four screen portions, the arcuate portion defined by the sizing window 432 would be 90° and if there were only two screen portions, the arcuate portion defined by the sizing window 432 would be 180°. Each sizing window 432 is generally defined by window ends 432a, 432b and can include a wiping member 433 located across the sizing window 432. The sizing shaft assembly 380 generally comprises an inner shaft 380a and an outer shaft 380b, said outer shaft body 380b being hollow and allowing for the inner shaft 380a to slide and turn within the outer shaft body 380b. The sizing shaft assembly 380 is operably, slidably mounted through a liquid end aperture 384 such that the sizing selector 382 remains proximate the open end 322. The sizing selector 382 can comprise a sizing indicia on 383 on an exterior surface 385 of the sizing selector 382, wherein the sizing indicia 383, including words such as, for example, micro, macro and nano or numbers such as 2.4, 1.2 and 0.6 can be arranged so as to provide a medical professional with an external, visual indication as to where the screen portions 378a, 378b, 378c are arranged across a cross-section of the body interior 332 and which of the screen portions 378a, 378b, 378c are open and exposed for flow by the sizing windows 432 on the sizing discs 430a, 430b. The porous sizing screen 378 can include one or more circumferential seal members 434 positioned around the circumference of the porous sizing screen 378 and interfacing with the body wall 346 to provide a fluid tight seal between the porous sizing screen 378 and the cylindrical body 302.

Figure 30:
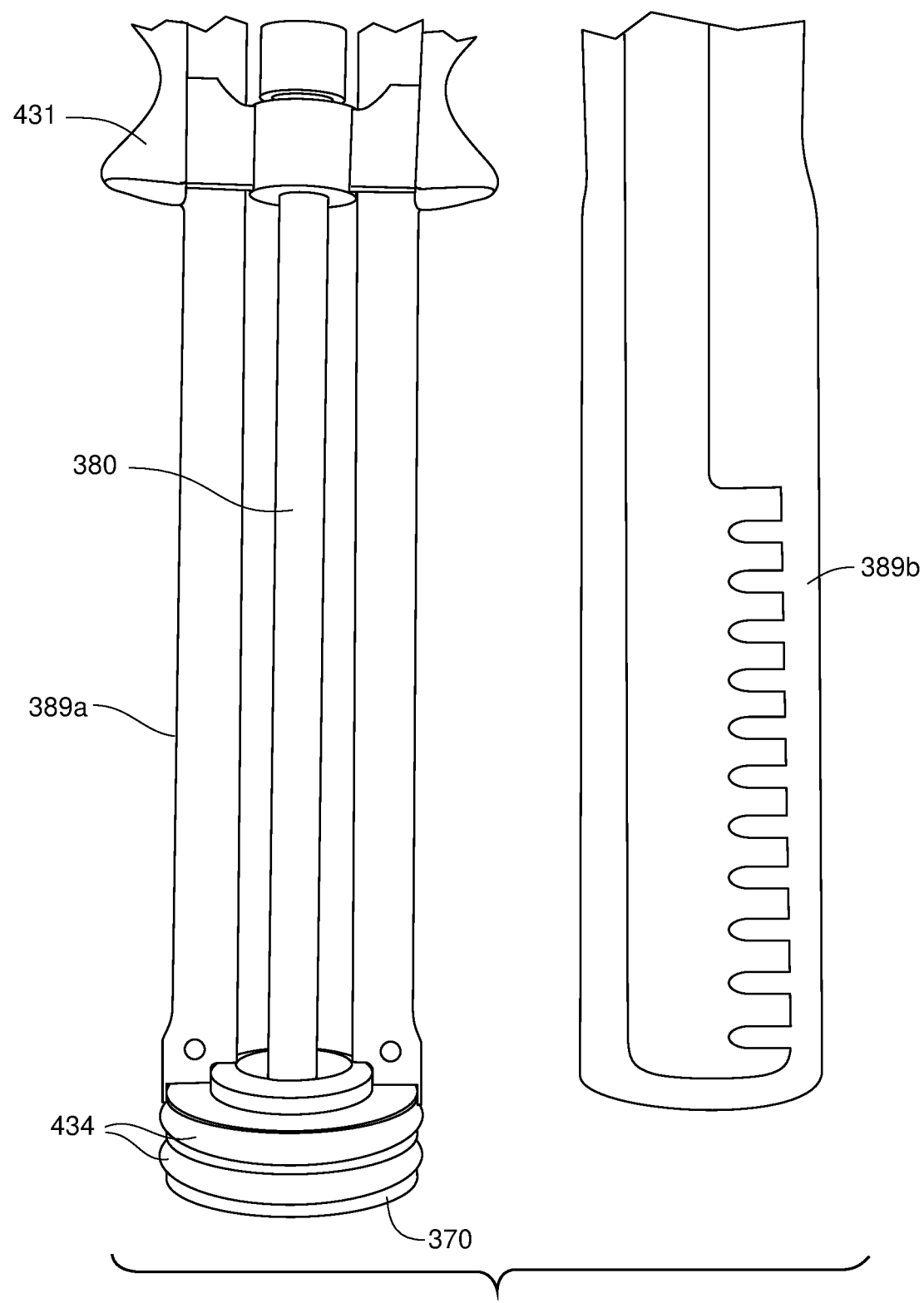
FIG. 30 is a side view of a disassembled cylindrical body for use with the fat harvesting assembly of FIG. 20A.
Figure 31:
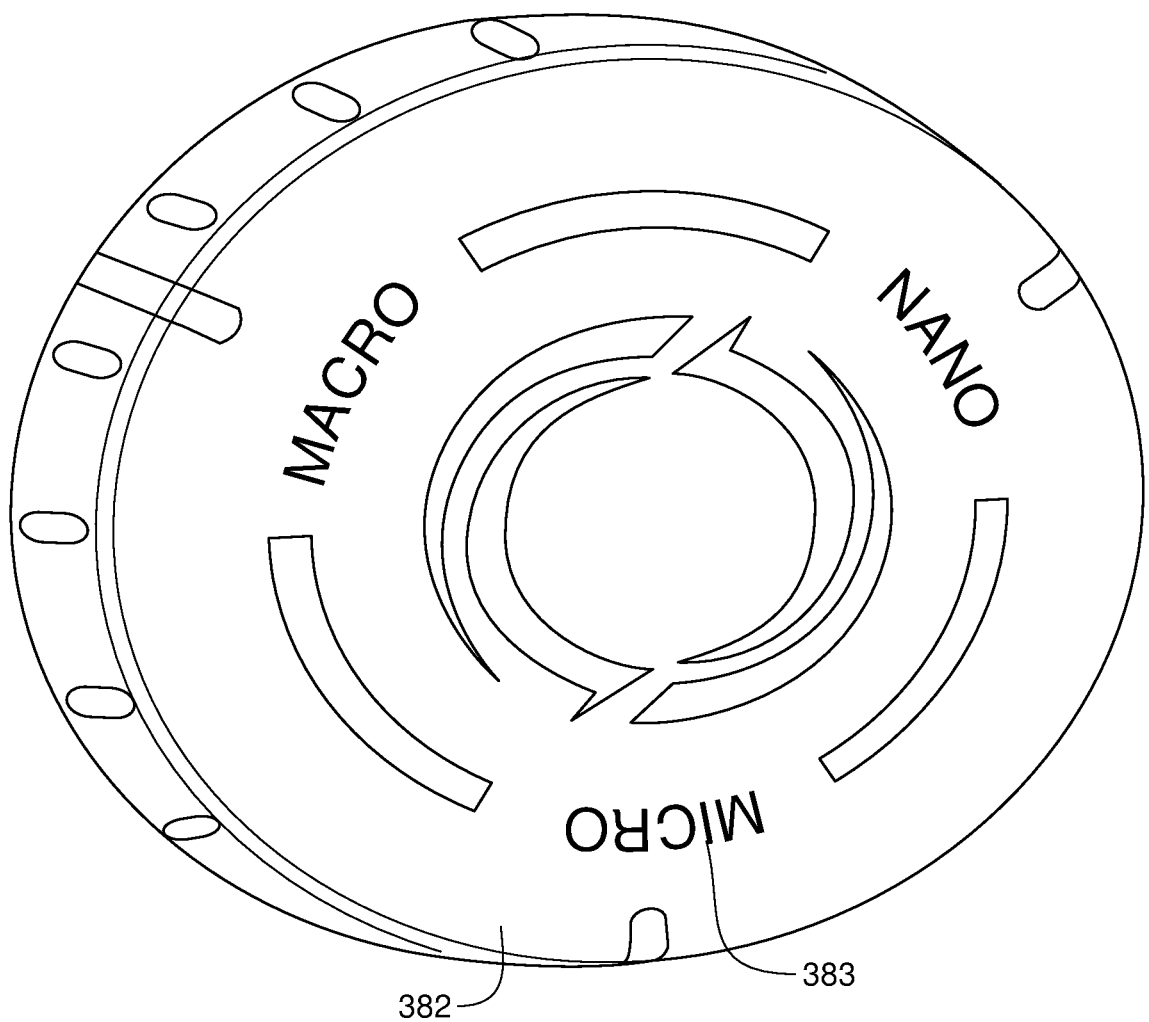
FIG. 31 is an end view of a sizing selector for use with the fat harvesting assembly of FIG. 20A

Plunger member 374 can further comprise a plunger body 389 having a locking channel 390 defined by a vertical channel 392 and a plurality of spaced apart horizontal channels 394 as seen in FIG. 30. Plunger body 389 can be formed from a pair of body members 389a, 389b that can be press-fit or otherwise coupled together. The sizing selector 382 is generally found at the biasing end 372 so as to allow the medical professional to press or pull on the sizing selector 382 to advance or retract the plunger member 374 within the cylindrical body 302. Generally speaking, plunger assembly 304 is slidably inserted into the cylindrical body 302 by directing the liquid end 370 into the plunger aperture 358. The locking channel 390 is positioned relative to the locking member 352 such that the locking post 356 resides within the vertical channel 392. The plunger assembly 304 can be advanced into the cylindrical body 302 such that the liquid end 370 approaches the floor cap 321. Plunger body 389 generally defines a hollow body interior 395 in which the sizing shaft assembly 380 resides and can be slidably advanced/retracted using the sizing shaft grip 431 such that the porous sizing screen 378 and sizing disc 430 can be moved away from the liquid end 370 such that the porous sizing screen 378 and sizing disc 430 can be advanced and/or retracted through the body interior 332 independent of the plunger member 374.

Generally, the method of harvesting face cells with the fat harvesting system 300 is similar to fat harvesting system 100. In a first harvesting step, the harvesting cannula 106 is attached to the cylindrical body 302 using the connector 110 and conduit connector 326a. The user then rotates the manual valve member 334 such that the first conduit 326 is open to fluid communication with the body interior 332 and the second conduit 328 is closed off. The user positions the needle tip 112 proximate a fat harvesting location such as the outer thigh and then inserts the needle tip 112 into the fat harvesting location. At this point, the medical professional can make their own preferential determination as to what harvesting mechanism to utilize.

For instance, the user can utilize plunger assembly 304 such that no external vacuum source is required during fat harvesting. While gripping the cylindrical body 302, the user can then pull on the sizing shaft grip 431 to begin withdrawing the plunger assembly 304 from the cylindrical body 302 to induce a vacuum condition within the body interior 332. The vacuum condition within body interior 332 is communicated through the first conduit 326 and ultimately to the needle tip 112. With a vacuum condition at needle tip 112, fat cells are suctioned through the harvesting cannula 106, into the first conduit 326 and ultimately into the body interior 332 where the user can compare the amount of fat cells recovered to the volumetric indicia 348. The medical professional can move the needle tip 112 within the fat harvesting location while continuing to withdraw the plunger assembly 304 until a desired volume of fat cells is recovered. Depending upon the reinjection location, it may be desirable to choose the cylindrical body 102 to have a desired maximum volume for the body interior 332, for example, 20 ml or 100 ml. Once the desired volume of fat cells has been recovered, the user can turn the manual valve member 334 such that the body interior 332 is closed off from the first conduit 326 and the second conduit 328 is in fluid communication with the body interior 132. The user can then advance the plunger assembly 304 back into the cylindrical body 302 to vent any accumulated air within the body interior 332 out the second conduit 328. With the air vented from the body interior 332, the user can turn the manual valve member 334 such that the body interior 332 is closed off from the first conduit 36 and second conduit 328 so as to avoid loss of the recovered fat cells. The user can then detach the harvesting cannula 106 from the first conduit 326 and appropriately dispose of the harvesting cannula 106.

In the event that the fat harvesting system 300 is utilized in an operating room with an available vacuum source, the step of withdrawing the plunger assembly 304 to induce a suction condition within the cylindrical body 302 can alternatively be replaced with connecting the available vacuum source to the vacuum port 361. When utilizing the vacuum source, the user would simply slide the plunger assembly 304 past the vacuum port 361 to create a desired open volume with the body interior 332 and utilize the vacuum source to draw fat cells through the harvesting cannula 106 until the desired volume of fat cells is harvested. At that point, the user could remove the vacuum source and the recovery and sizing procedure could otherwise proceed. If the medical professional has access to and the preference of using a powered liposuction device, the powered liposuction device can replace the harvesting cannula 106 and the powered liposuction device can be directly, fluidly coupled to the conduit connector 326a, whereby recovered fat cells can be introduced to the body interior 332 through the first conduit 326.

Once the fat cells have been harvested, regardless of the harvesting mechanism, the user can then position the cylindrical body 302 such that the treatment end 320 is placed into the decanting cavity 220 and the cylindrical body 302 is held in a vertical position similar to that shown in FIG. 16 with respect to cylindrical body 102. With the cylindrical body 302 in the vertical position, the harvested fat cells within the body interior 332 will then begin to separate and form distinct layers based upon the specific gravity of the various biological components. For example, an oil layer including the recovered fat cells and free lipids are generally less dense than a water layer such that the oil layer will generally form above the water layer with the cylindrical body 302 in the vertical position.

Once the oil and water layers have formed in the decanting step, the medical professional can expel the water layer from the cylindrical body 302. Generally, the oil/water interface is easily visible and once this interface is formed, a user can expel the water layer in one or more ways based upon the preferences of the medical professional. For instance, the medical professional can utilize the plunger assembly 304 or alternatively, an available wall suction source to expel the water layer. In the case of plunger assembly 304, the user can advance the advance the plunger assembly 304 into the cylindrical body 302 such that water layer is evacuated out the treatment end 320, either through the porous floor screen 340 or out the flow conduit 324. If the water layer is evacuated out of the porous floor screen 340, the user simply unlatches the latch assembly 408 and rotates the floor cap 321 to an open position exposing the porous floor screen 340 and floor opening 342. If the water layer is evacuated out of the flow conduit 324, the manual valve member 334 is rotated to open either the first conduit 326 or second conduit 328 for evacuating the water layer out of the associated conduit connector 326a, 328a. In the event that wall suction is utilized, the suction source is attached to the vacuum port 361 and the water layer can be removed through the vacuum port 361. In some instances, the medical professional may choose to simply detach the floor cap 321 from the cylindrical body 302 by rotatably disengaging the internal thread 406 from the external thread 400 whereby the water layer can simply be poured from the now open cylindrical body 302. Once the water layer has been evacuated from the body interior 332, the user then closes off the evacuation path by, for example, closing and relating the rotatable cover 306, closing the manual valve member 334, removing the suction source from the vacuum port 361 or by rotatably reattaching the floor cap 321 to the cylindrical body 302.

With the water layer removed from the body interior 332, the user can then wash the recovered fat cells to remove any remaining biological impurities. Generally, saline can be introduced in a variety of ways including, for example, though the vacuum port 361 or through the flow conduit 324. With the saline introduced in the body interior 332, the oily/water interface will form again and the resulting water (saline) layer can removed using any of the variety of expelling steps previously discussed. The saline washing step can repeated as many times as desired by the medical professional.

With the recovered fat cells having being been washed and separating, the process of morcellizing or sizing the washed fat cell can commence. Generally, the user locks the position of the plunger assembly 304 relative to the cylindrical body 302 by rotating the plunger member 374 such that the locking post 356 slides into one of the horizontal channels 394. With the locking post 356 retained within one of the horizontal channels 394, the plunger member 374 is prevented from being inserted or withdrawn relative to the cylindrical body 302. With the positon of the plunger member 374 fixed relative to the cylindrical body 302, the user can grasp the sizing shaft grip 431 and advance the porous sizing screen 378 back and forth through the recovered fat cells within the cylindrical body 302.

Depending on the experience and preferences of the medical professional relative to where the recovered fat cells are to be later reinjected, the medical professional can rotate the sizing selector 328 such that the sizing discs 430a, 430b are positioned with their sizing windows 432 exposing the desired one of screen portions 378a, 378b or 378c. Thus as the porous sizing screen 378 is directed back and forth through the body interior 332, the recovered fat cells are forced through the screen openings of the selected screen portion 378a, 378b or 378c. In some instances, the medical professional may start with the screen portion 378a having the largest screen openings and then use the sizing selector 382 to choose to screen portion 378b having the next largest screen openings followed by using the sizing selector 328 to choose the screen portion 378c having the smallest screen openings. In this way, the medical professional can use a multi-step sizing process to achieve sequentially smaller fat cells.

As the porous sizing screen 378 is directed back and forth through the body interior 332, biological components such as fat cells, can collect on the surface and being plugging the screen openings of the porous sizing screen 378 such that it can become increasingly difficult to move the porous sizing screen 378 within the cylindrical body 302. Using the sizing selector 382, the user can rotate the sizing discs 430a, 430 relative to the porous sizing screen 378 whereby the window ends 432a, 432b and wiping member 433 are rotatably wiped across the screen portions 378a, 378b, 378c on both sides of the porous sizing screen, whereby any accumulated or plugged biological material is dislodged and removed from the screen openings in the screen portions 378a, 378b, 378c. This wiping step can be repeated multiple times during the sizing process. In addition, moving the porous sizing screen 378 back and forth through the cylindrical body 302 causes the one or more circumferential seal members 434 to wipe and removed any biological material that accumulates on the body wall 346 or on the vacuum port 361.

Once the fat cells have been morcellized/sized, they are now ready for reinjection within a desired location of the body. One or more injections syringes 230 can be attached to conduit connector 326a and filled though the first conduit 324.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A fat harvesting system, comprising:
   a reservoir body having an input fluid connector to receive bodily fluid including fat cells from a liposuction device so that the bodily fluid is deliverable into a reservoir body, the reservoir body including volumetric indicia to identify a volume of the bodily fluid received in the reservoir body;
   a vacuum port in communication with the reservoir body at a position to remove a separated aqueous layer of the bodily fluid while a harvested fat layer including the fat cells remains in the reservoir body;
   a wiper rotatably mounted within the reservoir body so as to rotate about an axis of the reservoir body in response to movement of an actuator external to the reservoir body;
   an extraction syringe matable with a conduit connector of the reservoir body to withdraw at least a portion of the fat cells from the reservoir body;
   an adjustable sizing screen having a plurality of arcuate screen portions that are movable relative to the reservoir body so that said portion of the fat cells advance through a selected one of the arcuate screen portions before reaching the extraction syringe, wherein a first arcuate screen portion of the plurality of arcuate screen portions of the adjustable sizing screen has a first screen opening size, and a second arcuate screen portion of the plurality of arcuate screen portions of the adjustable sizing screen has a second screen opening size that is smaller than the first screen opening size; and
   a size selector knob that is rotatable relative to the reservoir body so that the selected one of the arcuate screen portions is positioned to contact said portion of the fat cells.

2. The fat harvesting system of claim 1, wherein the first screen opening size is 2.4 mm, and the second screen opening size is 1.2 mm.

3. The fat harvesting system of claim 1, wherein the reservoir body comprises a cylindrical sidewall and the adjustable sizing screen has a circular periphery.

4. The fat harvesting system of claim 3, wherein each arcuate screen portion is a 120-degree arcuate portion of the adjustable sizing screen.

5. The fat harvesting system of claim 1, wherein the wiper comprises a wipe blade that is mounted to a shaft configured to rotate within the reservoir body in response to rotation of the actuator external to the reservoir body.

6. The fat harvesting system of claim 5, wherein the wiper is configured to dislodge accumulated biological material from screen openings located adjacent to the wipe blade.

7. The fat harvesting system of claim 1, wherein the vacuum port is laterally offset from a cylindrical sidewall of the reservoir body.

8. The fat harvesting system of claim 1, wherein a distal tip of the extraction syringe is releasable from the conduit connector so that said portion of the fat cells are transferable to a reinjection site.

9. The fat harvesting system of claim 8, further comprising an additional extraction syringe that is releasably matable to the conduit connector to withdraw a second portion of the fat cells from the reservoir body.

10. The fat harvesting system of claim 1, wherein the adjustable sizing screen is positioned between an interior volume of the reservoir body and the conduit connector matable to the extraction syringe.

11. The fat harvesting system of claim 1, wherein the reservoir body has a longitudinal length that is greater than a lateral width, and the reservoir body is positioned with the longitudinal length in a vertical orientation for decanting the separated aqueous layer of the bodily fluid from the harvested fat layer within the reservoir body.

12. The fat harvesting system of claim 1, further comprising a wash introduction path in communication with the reservoir body to receive a wash fluid into the body reservoir so that the wash fluid contacts the harvested fat layer including the fat cells.

13. The fat harvesting system of claim 1, further comprising a manually adjustable valve member spaced apart from the reservoir body and movable to at least a first fluid connection position, a second fluid connection position, and an off position.

14. The fat harvesting system of claim 1, wherein the fat harvesting system is a sterilized, single-use kit.

* * * * *